United States Patent [19]

Nocka et al.

[11] Patent Number: 5,525,708
[45] Date of Patent: Jun. 11, 1996

[54] COVALENT DIMER OF KIT LIGAND

[75] Inventors: Karl H. Nocka, Harvard; Robert B. Lobell, Watertown, both of Mass.

[73] Assignee: CytoMed, Inc., Cambridge, Mass.

[21] Appl. No.: 220,379

[22] Filed: Mar. 28, 1994

[51] Int. Cl.$^6$ ..................................................... C07K 14/52
[52] U.S. Cl. ........................ 530/409; 530/351; 530/399; 530/417
[58] Field of Search .............................. 435/69.1, 252.33, 435/320.1; 530/350, 351, 399, 412, 417, 402, 404, 409

[56] References Cited

U.S. PATENT DOCUMENTS 4,873,191  10/1989  Wagner ................................ 435/172.3
5,199,942  4/1993   Gillis ..................................... 604/4

FOREIGN PATENT DOCUMENTS 0423980    10/1990  European Pat. Off. .
WP93/05795  5/1991  WIPO .
WO92/00376  1/1992  WIPO .
WO92/03459  3/1992  WIPO .
WO93/21936 11/1993  WIPO .

OTHER PUBLICATIONS

Alter, B. P., et al., "Effect of Stem Cell Factor on In Vitro Erythropoiesis in Patients With Bone Marrow Failure Syndromes", Biog. 8013000–3008 (1992).
Anderson, D. M., et al., "Molecular Cloning of Mast Cell Growth Factor, a Hematopoietin that is Active in Both Membrane Bound and Soluble Forms", Cell, 63:235–243 (1990).
Andrews, R. G., et al., "A c-kit Ligand, Recombinant Human Stem Cell Factor, Mediates Reversible Expansion of Multiple CD34$^{+\cdot}$ Colony-forming Cell Types in Blood and Marrow of Baboons", Blood, 80(4):920–927 (1992).
Andrews, R. G., et al., "The Ligand for c-kit, Stem Cell Factor, Stimulates the Circulation of Cells That Engraft Lethally Irradiated Baboons", Blood, 80(11):2715 (1992).
Andrews, R. G., et al., "Recombinant Human Stem Cell Factor, a c-kit Ligand, Stimulates Hematopoiesis in Primates", Blood, 78(8):1975–1980 (1991).
Arakawa, T., et al., "Glycosylated and Unglycosylated Recombinant–derived Human Stem Cell Factors are Dimeric and Have Extensive Regular Secondary Structure", The Journal of Biological Chemistry, 266:18942–18948 (1991).
Aruffo, A., et al., "CD44 is the Principal Cell Surface Receptor for Hyaluronate", Cell, 61:1303–1313 (1990).
Barzan, J. F., "Generic and Structural Homology of Stem Cell Factor and Macrophase Colony–Stimulating Factor", Cell, 65;9–10 (1991).
Bischoff, S. C., et al., "c-kit Ligand: A Unique Potentiator of mediator Release by Human Lung Mast Cells", J. Exp. Med., 175:237–244) (1992).
Bodine, D. M., et al., "In Vivo Administration of Stem Cell Factor to Mice Increases the Absolute Number of Pluripotent Hematopoietic Stem Cells", Blood, 82:445–455 (1993).

Bradley, "Production and Analysis of Chimaeric Mice" in Teratocarcinomas and embryonic stem cells: A practical approach E. J. Robertson, ed. pp. 113–151 (Oxford, Washington, D.C. IRL Press 1987).
Briddell, R. A., et al., "Effect of c-kit Ligand on In Vitro Human Megakaryocytopoiesis", Blood, 78(11):904–911 (1991).
Briddell, R. A., et al., "Recombinant Rat Stem Cell Factor Synergizes with Recombinant Human Granulocyte Colony-–Stimulating Factor In Vivo in Mice to Mobilize Peripheral Blood Progenitor Cells that Have Enhanced Repopulating Potential", Blood, 82(6):1720–1723 (1993).
Brosius, J., et al., "Regulation of Ribosomal RNA Promoters with a Synthetic lac Operator", Proc. Natl. Acad. Sci. USA, 81:6929–6933 (1984).
Coleman, et al., "Regulation of Mouse Peritoneal Mast Cell Secretory Function by Stem Cell Factor, IL–3 or IL–4$^1$, J. Immunol.", 150(2):556–562 (1993).
Columbo, M., et al., "The Human Recombinant c-kit Receptor Ligand, rhSCF, Induces Mediator Release from Human Cutaneous Mast Cells and Enhances IgE–dependent Mediator Release from Both Skin Mast Cells and Peripheral Blood Basophils", J. Immunol., 149(2):599–608 (1992).
Copeland, N. G., et al., "Mast Cell Growth Factor Maps Near the Steel Locus on Mouse Chromosome 10 and is Deleted in a Number of Steel Alleles", Cell, 63:175–183 (1990).
Crawford, I., et al., "A Phase 1 Trail of Recombinant Methionyl Human Stem Cell Factor (SCF) in Patients (PTS) with Advanced Non–Small Cell Lung Carcinoma INSCL)", Proc. Am. Soc. Clin. Oncol., 12:135 (1993).
Demetri, G., et al., "A Phase I Trial of Recombinant Methionyl Human Stem Cell Factor (SCF) in Patients with Advanced Breast Carcinoma Pre– and Post–Chemotherary (CHEMO) with Cyclophosphamide (C) and Doxorubicin", Proc. Amer. Soc. Clin. Oncol., 12:142 (1993).
deVries, P., et al., "The Effect of Recombinant Mast Cell Growth Factor on Purified Murine Hematopoietic Stem Cells", J. Exp. Med., 173:1205 (1991).
Flanagan, J. G., et al., "Transmembrane Form of the kit Ligand Growth Factor is Determined by Alternative Splicing and is Missing in the S/$^d$ Mutant", Cell, 64:1025–1035 (1991).

(List continued on next page.)

Primary Examiner—Marianne P. Allen
Attorney, Agent, or Firm—Fish & Neave; James F. Haley, Jr.; Andrew S. Marks

[57] ABSTRACT

A modified form of KL, the ligand for the c-Kit proto-oncogene, has been prepared wherein the protein is stabilized by an intermolecular covalent linkage. The protein can be prepared by expression of a recombinant protein which is dissolved in denaturant and refolded under conditions resulting in a disulfide linked dimer. Examples demonstrate the purification and characterization of this disulfide-linked cysteine dimer kit ligand (KL-CD) which contains at least one intermolecular disulfide bond and has at least ten-fold greater activity in promoting cell proliferation than native, non-covalently linked KL, as measured in in vitro assays.

5 Claims, 7 Drawing Sheets

OTHER PUBLICATIONS

Gorman, C., et al., "High Efficiency DNA–Mediated Transformation of Primate Cells", *Science*, 221:551–553 (1993).

Hantzopoulos et al., 1989 "Improved gene expression upon transfer of the adenosine deaminase minigene outside the transcriptional unit of a retroviral vector", *Proc. Natl. Acad. Sci. USA*, 86:3519–3523.

Huang, E. J. et al., "The Hematopoietic Growth Factor KL is Encoded by the S/Locus and is the Ligand of the c–kit Receptor, the Gene Product of the W Locus", *Cell*, 63:225–233 (1990).

Huang, E. J., et al., "Differential Expression and Processing of Two Cell Associated Forms of the Kit–Ligand": KL–1 and KL–2, *Molecular Biology of the Cell*, 3:349–362 (1992).

Hunt, P., et al., "Evidence That Stem Cell Factor is Involved in the Rebound Thrombocytosis That Follows 5–Fluoroucil Treatment", *Blood*, 80(4):904–911 (1992).

Juttner, C. A., et al., "Comparison of Haematological Recovery, Toxicity and Supportive Care of Autologous PBSC, Autologous BM and Allogeneic BM Transplants", *Int. J. Cell Cloning*, 10:160 (1992).

Kawasaki, E. S., et al., "Molecular Cloning of a Complementary DNA Encoding Human Macrophage–Specific Colony–Stimulating Factor (CSF–1)", *Science*, 230:291–296 (1985).

Khosla, C., et al., "Expression of Recombinant Proteins in *Escherichia coli* Using an Oxygen–Responsive Promoter", *Bio Technology*, 8:554–558 (1990).

Kohn et al., 1987 "Retroviral–mediated gene transfer into mammalian cells", *Blood Cells*, 13:285–298.

Langley, K. E., et al., "Purification and Characterization of Soluble Forms of Human and Rat Stem Cell Factor Recombinantly Expressed by *Escherichia coli* and by Chinese Hamster Ovary Cells", *Archives of Biochemistry and Biophysics*, 295(1):21–28 (1992).

Law, M–F., et al., "A Stable Bovine Papillomavirus Hybrid Plasmid That Expresses a Dominant Selective Trait", *Mol. Cell. Biol.*, 3:2110–2115 (1983).

Lee, F., et al., "Glucocorticoids Regulate Expression of Dihydrofolate Reductase cDNA in Mouse Mammary Tumor Virus Chimaeric Plasmids", *Nature*, 294:28–232 (1981).

Lindsley, P. S., et al., "CTLA–4 is a Second Receptor for the B Cell Activation Antigen B7", *J. Exp. Med.*, 174:561–569 (1991).

Lu, et al., "Amino Acid Sequence and Post–translational Modification of Stem Cell Factor Isolated from Buffalo Rat Liver Cell–conditioned Medium", *J. Biol. Chem.*, 266(13):8102–8107 (1991).

Lyman, S. D., et al., "Molecular Cloning of a Ligand for the flt3/flk–2 Tyrosine Kinase Receptor: A Proliferative Factor for Primitive Hematopoietic Cells", *Cell*, 75:1157–1167 (1993).

Martin, F. H. et al., "Primary Structure and Functional Expression of Rat and Human Stem Cell Factor DNAs", *Cell*, 63:203–211 (1990).

McKniece, I. K., et al., "Recombinant Human Stem Cell Factor Syneraises with GM–CSF, G–CSF, IL–3 and Epo to Stimulate Human Progenitor Cells of the Myeloid and Erythroid Lineages", *Exp. Hematol.*, 19:226–231 (1991).

McMahon, A. P., et al., "The Wnt–1 (int–1) Proto–Oncogene is Required for Development of a Large Region of the Mouse Brain", *Cell*, 62:1073–1085 (1991).

Metcalf, D., et al., "Direct Proliferative Actions of Stem Cell Factor on Murine Bone Marrow Cells In Vitro: Effects of Combination with Colony–Stimulating Factors", *Proc. Natl. Acad. Sci. USA*, 88:6239–6243 (1991).

Molineux, G., et al. "The Effects on Hematopoiesis of Recombinant Stem Cell Factor Administered in Vivo to Mice Either Alone or in Combination Colony–Stimulating Factor", *Blood*, 78(4):916–966 (1991).

Mott, J. E., et al., "Maximizing Gene Expression From Plasmid Vectors Containing the $\lambda$ $P_1$ Promoter: Strategies for Overproducing Transcription Termination Factor p", *Proc. Natl. Acad. Sci. USA*, 82:88–92 (1985).

Nakajima, K., et al., "Stem Cell Factor has Histamine Releasing Activity in Rat Connective Tissue–type Mast Cells", *Biochem, Biophys. Res. Comm.*, 183(3):1076–1083 (1992).

Nocka, K., et al., "Candidate Ligand for the c–kit Transmembrane Kinase Receptor: KL, a Fibroblast Derived Growth Factor Stimulates Mast Cells and Erythroid Progenitors", *EMBO J.*, 9(10):3287–3294 (1990).

Reed, R. R., "Transposon–Mediated Site–Specific Recombination: A Defined in Vitro System", *Cell*, 25, 713–719 (1981).

Rettenmeir, C. W., et al., "Differential Processing of Colony–Stimulating Factor 1 Precursors Encoded by Two Human cDNAs", *Mol. Cell. Biol.*, 8(11):5026–5034 (1988).

Robertson, E. J. "Embryo–Derived Stem Cell Lnes" In: Teratocarcinomas and Ebryonic Sem Clls: A Pactical Aproach, E. J. Robertson, ed. 71–112 (Oxford–Washington, D.C.: IRL Press, 1987).

Sarver, N., et al., "Bovine Papilloma Virus Deoxyribonucleic Acid: A Novel Eucaryotic Cloning Vector", *Mol. Cell. Biol.*, 1:486–496 (1981).

Sarver, N., et al., "Transformation and Replication in Mouse Cells of a Bovine Papillomavirus–pML2 Plasmid Vector that can be rescued in Bacteria", *Proc. Natl. Acad. Sci., USA*, 79:7147–7151 (1982).

Shimatake, H., et al., "Purified $\lambda$ Regulatory Protein cII Positively Activates Promoters for Lysogenic Development", *Nature*, 292:128–132 (1981).

Sprague, J., et al., "Expression of a Recombinant DNA Gene Coding for the Vesicular Stomatitis Virus Nucleocapsid Protein", *J. Virol.*, 45:773–781 (1983).

Templeton, D., et al. "N–Terminal Amino Acid Sequences of the Polyoma Middle–Size T Antigen Are Important for Protein Kinase Activity and Cell Transformation", *Mol. Cell. Biol.*, 4(5):817–821 (1984).

Williams, D. E., et al., "Identification of a Ligand for the c–kit Proto–Oncogene", *Cell*, 63:167–174 (1990).

Williams, L. T., "Signal Transduction by the Platelet––Derived Growth Factor Recaptor", *Science*, 243:1564–1570 (1989).

Wong, G. G., et al., "Human CSF–1: Molecular Cloning and Expression of 4kb cDNA Encoding the Human Urinary Protein", *Science*, 235:1504–1508 (1987).

Yung, Y. P., et al., "Long–Term in Vitro Culture of Murine Mast Cells", *J. Immunol.*, 129(3):1256–1261 (1982).

Zinn, K., et al., "Identification of Two Distinct Regulatory Regions Adjacent to the Human β–Interferon Gene", *Cell*, 34:865–879 (1983).

Zsebo, K. M., et al., "Identification, Purification, and Biological Characterization of Hematopoietic Stem Cell Factor from Buffalo Rat Liver–Conditioned Medium", *Cell*, 63:195–201 (1990).

Zsebo, K. M., et al., "Radioprotection of Mice by Recombinant Rat Stem Cell Factor", *Blood*, 89:9464–9468 (1992).

Zsebo, K. M., et al., "Stem Cell Factor is Encoded at the S/Locus of the Mouse and is the Ligand for the c–kit Tyrosine Kinase Receptor", *Cell*, 63:213–214 (1990).

COVALENT DIMER OF KIT LIGAND

BACKGROUND OF THE INVENTION

The present invention is directed to the method of production and therapeutic application of a covalent dimer of the cytokine kit ligand with increased proliferative activity.

Kit ligand (KL) is a growth and differentiation factor for an assortment of cell types, and is known to be a ligand for the c-kit proto-oncogene. KL was initially identified based on a variety of biological activities and has therefore been referred to by different names, including Stem Cell Factor, Mast Cell Growth Factor, and more recently Steel Factor, in recognition of the gene locus in the mouse which encodes KL, as described by Anderson, et al., (1990) *Cell* 63,235–243; Huang, E., et al. (1990) *Cell* 63, 225–233; Martin, et al. (1990) *Cell* 63,203–211; Nocka, et al., (1990) *EMBO J.* 9, 3287–3294; Williams, et al., (1990) *Cell* 63,167–174; Zsebo, et al. (1990) *Cell* 63, 195–201; Zsebo, K. M., et al., (1990) *Cell* 63, 213–214.

The ability of KL to promote the proliferation of a variety of cell types indicates that KL is useful as a therapeutic in a variety of clinical indications where enhanced hematopoietic recovery would be beneficial. For example, KL stimulates the survival and proliferation of immature hematopoietic stem cells and progenitor cells, as reported by deVries, et al. (1991) *J. Exp. Med.* 173, 1205; McKniece, et al., (1991) *Exp. Hematol.* 19, 226–231; Metcalf, et al., *Proc. Natl. Acad. Sci. USA* 88, 6239–6243; Nocka, et al. (1990) *EMBO J.* 9, 3287–3294. Thus, KL could be used for the ex vivo expansion of stem cells and progenitors from donor bone marrow prior to transplantation, as proposed in U.S. Pat. No. 5,199,942 to Gillis. KL also acts on erythroid progenitors, and in combination with erythropoietin, drives their differentiation, as reported by Nocka, et al., (1990). This property should make KL useful in treating anemias such as that associated with patients having Diamond Blackfan Syndrome, described by Alter, et al., (1992) *Blood* 80, 3000–3008. KL is also a potent growth factor for megakaryocytic progenitors and in combination with late acting thrombopoietic factors such as IL-6, stimulates megakaryocytic differentiation, as reported by Briddell (1991), *Blood* 78, 904–911. KL could thus be useful in stimulating megakaryocyte proliferation and platelet production in thrombocytopenic patients Andrews, et al., (1992) *Blood* 80, 920–927; Hunt, et al., (1992) *Blood* 80, 904–911. KL has also been shown to be a potent cytokine in the mobilization of stem cells from the bone marrow to the peripheral blood and, in combination with G-CSF, results in significantly greater numbers of progenitor cells than are mobilized through other treatments, as reported by Andrews, et al., (1992) *Blood* 80, 920–927; Molineux, et al., (1991) *Blood* 78, 961; Andrews, et al., (1992) *Blood* 80, 2715; Briddell, et al., (1993) *Blood* 82, 1720–1723. Stem cells and progenitors that have first been mobilized and then collected from the peripheral blood have been shown by Juttner, et al. (1992) *Int. J. Cell Cloning* 10, 160, to be useful either alone or in combination with a bone marrow transplant to speed hematopoietic recovery post radio/chemotherapy.

While KL has many properties which make it a potentially useful therapeutic, KL also acts as a mast cell priming factor and secretagogue, promoting the release of mast cell-derived proinflammatory mediators which can lead not only to local tissue inflammation but more dangerously, to systemic anaphylaxis, as observed by Coleman, et al., (1993) *J. Immunol.* 150, 556–562; Columbo, et al., (1992) *J. Immunol.* 149, 599–608; and Nakajima, et al., (1992) *Biochem. Biophys. Res. Comm.* 183, 1076–1083. The mast cell activating property of KL has been shown to limit the therapeutic potential of native KL. In phase one clinical trials by Amgen of KL administered to patients undergoing chemotherapy, a significant number of patients experienced anaphylactic episodes in response to the KL therapy, mandating their removal from the KL treatment Crawford, et al., (1993) *Proc. Am. Soc. Clin. Oncol.* 12,135; Demetri, et al., (1993) *Proc. Amer. Soc. Clin Oncol.* 12, 142. Patients that received lower doses of KL, less than 25 µg/kg/day, exhibited minimal side effects; however, at this dose range, KL alone provides little benefit in terms of hematopoietic recovery or peripheral blood progenitor mobilization.

KL, and the receptor to which it binds, the proto-oncogene c-kit, are considered to be members of the Platelet Derived Growth Factor (PDGF) family. Members of this family have several common features, including the structure of the ligands, described by Nocka, et al., (1990); Flanagan, et al., (1991) *Cell* 64, 1125–1135; Huang, et al., (1992); Bazan (1991) *Cell* 65, 9–10; Huang, et al., (1990) and the structure and mechanism of action of the receptors, as described by Williams, et al., (1990) *Cell* 63, 167–174.

The synthesis and expression of KL is similar to other members of the PDGF family, particularly colony stimulating factor-I (CSF-1 or Macrophage-CSF (M-CSF)) Kawasaki, E. S., et al., (1985) *Science* 230, 291–296; Wong, G. G., et al., (1987) *Science* 235, 1504–1508, and the recently identified ligand for the Flt-3/Flk-2 receptor Lyman, et al., (1993) *Cell* 75, 1157–1167. M-CSF is synthesized from multiple mRNA transcripts that encode for transmembrane proteins, but which lead to either a predominant cell surface bound CSF-1 molecule due to the lack of one proteolytic cleavage site, or to a soluble, proteolytically cleaved CSF-1. Rettenmeier, C. W., Roussel, M. F. (1988) *Mol. Cell. Biol.* 8, 5026–5034. Similarly, there are at least two naturally occurring forms of KL that arise due to alternative mRNA splicing, as reported by Anderson, et al. (1990), Flanagan, et al., (1991), and Huang, et al., (1992). Both forms are first synthesized as transmembrane proteins. The most abundant form (KL-1) gives rise to a protein of 45 kDa which has a proteolytic cleavage site at amino acids 164–165 (Martin, et al., (1990)), and is readily cleaved to give rise to a soluble protein subunit of 30–35 kDa (Huang, et al., (1992)). The second form of KL (KL-2) is derived from a message in which exon 6, encoding the proteolytic cleavage site, has been spliced out (Anderson, et al., (1990); Flanagan, J. G., et al., (1991) *Cell* 64, 1125–1135. Without this site a less efficient proteolytic site is used, and the majority of KL-2 remains as a cell surface protein (Flanagan, et al., (1991); Huang, et al, (1992)).

KL does not contain an intermolecular disulfide bond; although it occurs as a dimer when isolated, the units are held together solely by non-covalent interactions (Nocka, et al., (1990); Asakawa, *J. Biol. Chem.* 266, 18942–18948. Thus, as analyzed by gel filtration chromatography, soluble KL (KL-1) migrates as a dimer of approximately 60 kDa, when glycosylated or 40 kD when not glycosylated. However, when analyzed by SDS-PAGE under reducing or non-reducing conditions, native KL migrates with an apparent molecular weight of a monomer, between 30 and 35 kDa when glycosylated or between 18 and 20 kD when not glycosylated. It is unknown whether membrane associated KL, KL-2, exists in a dimeric state.

cDNA's encoding human, mouse, and rat KL have been cloned and expressed in mammalian, yeast and bacterial cells, as disclosed in PCT/US91/04272 by Immunex Corporation and PCT/US90/05548 by Amgen, Inc. The recombinant KL proteins have biological activity that is comparable to naturally occurring KL of the appropriate species. The protein has been shown to have intrachain disulfide bonds between cysteines at amino acid residues 4 and 89 and at residues 43 and 138, as described by Immunex and Amgen. As described by Amgen, when human KL was expressed as an insoluble protein in E. coli and refolded into active protein, the predominant form of the protein was a properly oxidized protein having a molecular weight of between 18,000 and 20,000 Da as determined under non-reducing conditions. A 37,000 Da protein was also observed under non-reduced conditions; however, no mention of biological activity was made. As reported by Immunex, mutants that were truncated to amino acid 138, that had the first two amino acids removed from the N-terminus, and that were missing the fifth glycosylation site were all active.

Recombinant KL from human and rodent preparations has been found to be as effective as the native molecules when assessed in a variety of in vitro hematopoietic assays. Lu, et al., (1991) *J. Biol. Chem.* 266, 8102–8107; Martin, et al., (1990) *Cell* 63,203–211; McKniece, et al., (1991) *Exp. Hematol.* 19, 226–231. The therapeutic potential of recombinant KL was suggested by its efficacy in several preclinical animal models. For example, administration of KL to rodents at dosages of 100 and 200 µg/kg/day led to significant increases in platelets, reticulocytes, and white blood cells, and to a dramatic increase in the number of circulating progenitor cells, as reported by Molineux, et al., (1991) *Blood* 78, 961; Bodine, et al., (1993) *Blood* 82, 45–455. Primate studies demonstrated a similar effect of KL on the hematopoietic system, as reported by Andrews, et al., (1991) *Blood* 78, 1975–1980. An important study in baboons demonstrated a dose-response effect of KL which mirrored effects seen in later clinical trials; KL had little effect on the hematopoietic system at dosages of between 10 and 25 µg/kg/day, but significant effect at between 100 and 200 µg/kg/day, as described by Andrews, et al., (1992) *Blood* 82, 920–927. Additionally, in a mouse irradiation model, pretreatment with KL rescued most of the animals exposed to a dose of radiation that was lethal to untreated animals, as described by Zsebo, et al. (1992) *Blood* 89, 9464–9468.

Although animal models suggested efficacy of KL in stimulating hematopoiesis, when assessed in a clinical trial for its ability to promote the mobilization of stem cells and myeloid progenitors from the bone marrow to the peripheral blood in patients who had received chemotherapy, significant toxicity, manifested as anaphylactic episodes or localized tissue inflammation, occurred in many patients in response to KL, as reported by Crawford, et al., (1993) *Proc. Am. Soc. Oncol.* 12, 135; Demetri, et al., (1993) *Proc. Amer. Soc. Clin. Oncol.* 12, 142. This toxicity was attributed to the mast cell priming-degranulating activity of KL, and occurred at dosages of 50 µg/kg/day or greater, below the dosage required for effective stem cell mobilization. Thus, native KL can be considered to possess an unfavorable "P:A" (cell proliferation:mast cell activation) ratio.

It is therefore an object of the present invention to provide a modified form of KL which shows increased potency in mediating cell proliferation in vitro, but no increase in its ability to promote mast cell priming.

It is a further object of the present invention to provide methods for making and using a modified KL having a more favorable P:A ratio which can stimulate hematopoietic recovery or stem cell/progenitor cell mobilization with less toxicity than native KL due to mast cell activation.

SUMMARY OF THE INVENTION

A modified ligand for c-kit proto-oncogene has been prepared wherein the protein is stabilized by intermolecular disulfide linkage between cysteine residues. This dimeric protein can be prepared by expression of a recombinant protein which is solubilized and refolded under conditions resulting in a covalently associated dimer. Native KL has cysteines at 4, 43, 89, and 138, and is believed to form intrachain bonds between 4 and 89 and 43 and 138. Examples demonstrate the purification and characterization of dimeric kit ligand (KL-CD) which has at least one intermolecular disulfide bond formed between one of the four cysteines in one monomer and one of the four cysteines in the other monomer.

BRIEF DESCRIPTION OF THE DRAWINGS

FIG. 1 is an alignment of the amino acid sequence of the soluble form of Kit Ligand from human (amino acids 1 to 164 of Sequence ID No. 2), murine (amino acids 1 to 164 of Sequence ID No. 6), and rat species (amino acids 1 to 164 of Sequence ID No. 4).

DETAILED DESCRIPTION OF THE INVENTION

Figure 2A:
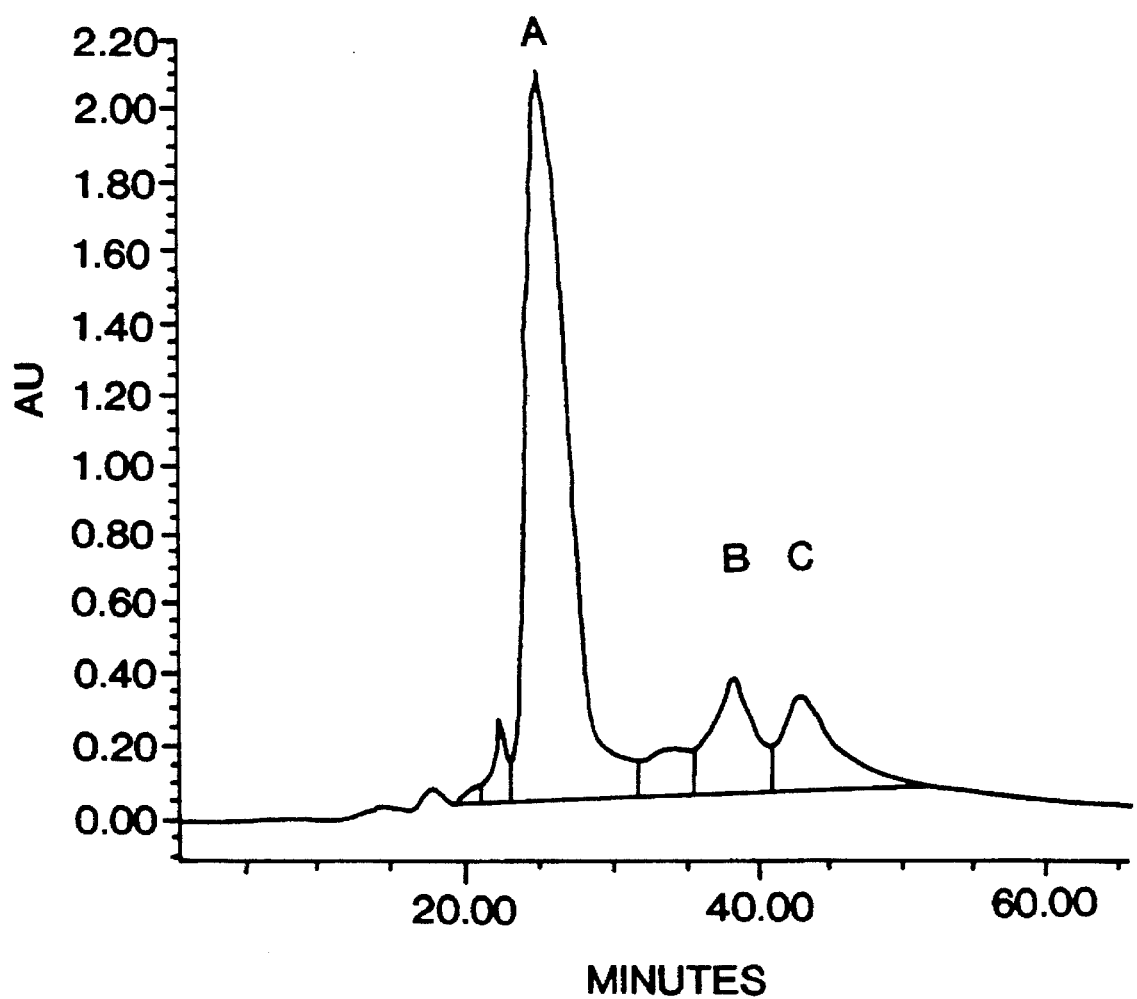
FIG. 2A is the elution profile from a first C18 column; where non-covalently linked mKL (KL-NC) elutes at approximately 38% n-propanol, KL-CD elutes at approximately 45% n-propanol, and a third peak containing a different form of KL-CD with very low activity elutes after the biologically active KL-CD peak.

As described herein, it has been discovered that it is possible to prepare a covalently crosslinked dimer of kit ligand, which differs from native KL in its relative ability to stimulate cell proliferation and mast cell degranulation. The modified KL is referred to herein as KL-CD, for KLcovalent dimer. Non-covalently linked KL is referred to herein as KL-NC.

Nucleotide and Amino Acid Sequences of Kit Ligand

The nucleotide sequence for murine kit ligand is shown in Sequence ID No.5; the corresponding amino acid sequence is shown in Sequence ID No. 6. The nucleotide sequence for human kit ligand is shown in Sequence ID No. 1; the corresponding human amino acid sequence is shown in Sequence ID No. 2.

Figure 1:
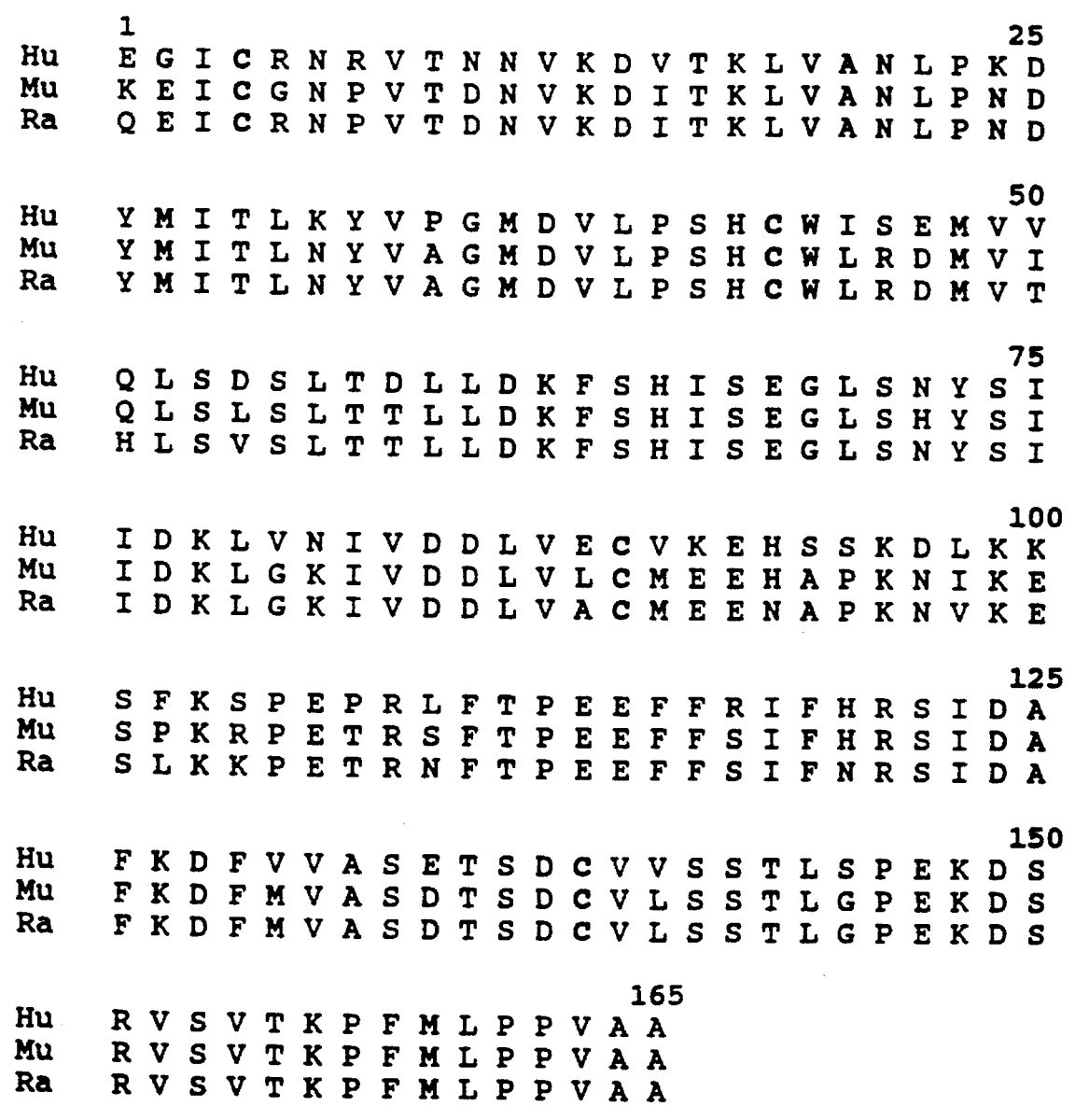

There is appreciable conservation at the primary sequence level among KL from the different species, in particular in the number and location of the cysteine residues, as shown by FIG. 1. Human (Sequence ID No. 2), murine (Sequence ID No. 6) and rat (Sequence ID No. 4) molecules are highly conserved at the amino acid level, with 79% 80% and 92% identity between human and mouse, human and rat, and mouse and rat, respectively. Furthermore, the number and location of the cysteines are absolutely conserved. Accordingly, the results shown in the examples for murine KL-CD may be extrapolated to human as well as other mammalian species of KL.

It is not necessary, and in fact is not preferred, to utilize the nucleotide sequence encoding the full length KL; in a preferred embodiment, the sequence encodes at least the first 138 amino acids, more preferably the first 162, 164, or 165 amino acids (minus the hydrophobic membrane binding region). Conservative substitutions, additions, and deletions based on differences in amino acid sequence using sequence alignment, as well as based on similarities in structure, charge, and chemistry, can be made to yield a functionally equivalent KL, referred to herein as KL, unless specifically noted otherwise.

Additional cysteines can be inserted in locations between the cysteines in the naturally occurring cysteines in order to form additional or alternative interchain covalent linkages, as described below.

Methods to make Covalently linked KL Dimers

In the preferred embodiment, dimers are made by expressing KL from a recombinant nucleotide sequence encoding KL which includes cysteine residues at positions corresponding to at least 4, 43, 89, and 138, denaturing the KL under conditions equivalent to between 4 and 12 M urea, most preferably 6 M urea, then refolding the proteins under conditions wherein the proteins form a covalently associated dimer, for example, in Tris™-HCl or phosphate buffered saline (PBS). Other modifications yielding KL-CD with altered biological activity can be produced as described below.

1. Formation of KL-CD having at least one interchain disulfide bond in place of at least one of the intrachain disulfide.

A preferred form of KL-CD described in Example 1 of this application contains at least one intermolecular disulfide bond in place of at least one of the intramolecular disulfide bonds found in KL-NC. This form of KL-CD has been demonstrated to be ten fold more potent than KL-NC in its ability to support the proliferation of a number of different types of cells. However, the mast cell priming/activating property of KL is not increased in the KL-CD molecule. This differential increase in growth stimulation in contrast to mast cell priming-activation of KL-CD is of utmost importance since the KL-induced anaphylaxis is presumably due to its action on mast cells. With native KL and KL-NC, ten fold more KL is required to stimulate maximal cell growth than is required to maximally prime mast cells for activation. In comparison, KL-CD is equipotent in its ability to stimulate cell growth as well as to prime mast cells for activation. The P:A ratio for KL-CD is thus ten fold more favorable than the P:A ratio of KL-NC.

KL-CD is also significantly more stable than KL-NC. The increased stability of KL-CD is particularly apparent at low concentrations, between 1 and 100 ng/ml, when incubated at 37° C. for several days to weeks. At these concentrations, significant loss in activity is observed for the recombinant KL-NC.

2. Deletion of one of the four cysteines in naturally occurring KL

A mutant KL dimer could also be formed as described above, where there is only one intrachain disulfide bond, by deletion of one of the cysteine residues not required for intrachain disulfide bond in KL-CD nor essential for biological activity.

Theoretically, the biologically active form of KL-CD, as described in Example 1, might consist of one intramolecular disulfide bond, one intermolecular disulfide, and one unpaired cysteine in each KL monomer. In this case, the cysteine residue not involved in a disulfide bond can be changed to another amino acid such as serine. Construction of this mutant cDNA could facilitate the formation of KL-CD with the same properties as the KL-CD described in Example 1. Since only one intramolecular disulfide bond could form from such a mutation, this mutation could result in a much greater yield of active KL-CD as compared to that in Example 1.

Specifically, covalent dimers of KL with desirable biological properties can be formed by the substitution of one of the other four cysteines (4, 43, 89 and 138), most preferably 43 or 138, with another amino acid, preferably serine. KL with any three of the four cysteines could fold into KL-CD with similar or different properties to that formed from KL with four cysteines.

3. Addition of one or more cysteines to naturally occurring KL

One or more cysteines can be added to KL to allow formation of additional intrachain or interchain disulfide bonds. For example, a fifth or additional cysteine(s) can be introduced into the cDNA to facilitate the formation of interchain disulfide bonds in addition to the two native intrachain disulfides. This interchain disulfide can be placed within a region of KL analogous to that of M-CSF. M-CSF contains an interchain disulfide formed between the cysteines at amino acid 31 in the two monomers, which is within the region where the two monomers are juxtaposed. Thus, mutation of an amino acid residue to cysteine within amino acids 18 to 30 of KL would be expected to generate a form of KL-CD with properties similar to that of the KL-CD described in example 1. More specifically, an additional amino acid such as another cysteine can be introduced between residues 25 and 26 since these residues must be interrupted by a single amino acid "space" in order to align the sequences of KL and M-CSF. (Bazan, F. (1991) *Cell* 65, 9–10). Alternatively, a location for an additional cysteine designed to yield an intermolecular disulfide bond can be determined through the elucidation of the disulfide pairs in the KL-CD described in Example 1.

4. Formation of KL fusion protein dimers

Covalent dimers or higher order multimers of KL with increased biological activity can be produced through the fusion of KL with heterologous proteins which contain covalent interactions with multiple subunits. An example of this is with immunoglobulin (Ig) Fc domain fusion proteins which have been used for the expression of a number of proteins as dimeric molecules, as described by Lindsley, P. S., et al. (1991) *J. Exp. Med.* 174, 561–569. In the Lindsley Ig fusion constructs, the gene encoding the protein of interest (CTLA-4) was fused to nucleotide sequences encoding the hinge, CH2 and CH3 domains of human Ig Cγ1. The resulting fusion protein formed soluble dimers and tetramers, which were disulfide linked through cysteines located in the CTLA-4 region. Those fusion proteins demonstrated CTLA-4 activity.

KL fusion proteins may also be generated for use in ex vivo cell culture, where the KL fusion proteins are immobilized to a solid substrate. This can be accomplished through the use of KL-Fc fusion proteins bound to Protein A beads. This can also be accomplished by the addition of a collagen binding domain to KL directly or via an Fc bridge so that KL can be coupled to collagen beads or coated substrates.

Methods for making soluble dimeric protein which is expressed on the host cell surface as a chimeric fusion protein incorporating the extracellular portion of the protein with the stem region of C4b binding protein (C4bp) are described in U.S. Ser. No. 08/118,366 filed Aug. 8, 1993.

In these constructs, the extracellular domain of CD28, a cell surface dimer, is fused to C-terminal 58 amino acids of C4 binding protein. When these constructs are expressed in mammalian cells, a multimeric CD28–C4bp protein is expressed on the cell surface. The protein can be cleaved from the multimeric surface protein to yield soluble protein. A dimeric protein can also be produced by expression of a plasmid vector incorporating the segments of the gene encoding placental alkaline phosphatase (PAP) adjacent to sequence encoding the extracellular region of the KL cDNA amino acids 1–164 or 165, and a lipid anchor, the cleavage site for a phospholipase, as described in PCT/US92/01867. In the constructs described in the '867 application the extracellular domain of CD28 is fused to the C-terminal 49 amino acids of PAP. When this construct is expressed, the C-terminal 30 amino acids of the PAP portion of the fusion protein are cleaved, leaving a C-terminal arginine residue. That arginine is then available for the addition of phosphatidylinositol glycan (pI-G). The pI-G acts as an anchor to hold the fusion protein to the cell membrane. Subsequent cleavage with phospholipase C releases soluble, dimeric CD28.

Stabilized dimers with increased biological activity can also be produced through non-covalent means by the fusion with domains that readily form stable hetero- or homomeric multimers. An example would be to use the so called "Leucine zipper" domain which will self associate with another protein that contains a Leucine zipper domain.

4. Formation of Chemically coupled KL dimers.

Chemical methods, not involving peptide or disulfide bond formation, which form a covalent bond between monomers may also be used to make KL dimers. Methods using a variety of commercially available bifunctional reagents that are available which crosslink proteins, for example, via free amino groups, can be utilized. The reagent DSS from Pierce Chemical Co., would be suitable for this purpose and its use is well known to those skilled in the art. Alternatively, the reagent BASED (Pierce) is a photoreactive crosslinker which reacts non-specifically and could be useful for crosslinking near the dimer interface of KL-NC.

Expression and isolation of KL-CD

KL-CD can be obtained by expression of the nucleotide sequence encoding KL in an appropriate procaryotic or eucaryotic expression system, for example, E. coli, followed by unfolding in urea and refolding in a more physiological buffer.

The formation of KL-CD through expression in mammalian and other eukaryotic species is demonstrated in Example 1. The protein can also be expressed in mammalian, yeast or insect cells, then purified and subsequently denatured and refolded to facilitate intermolecular disulfide bond formation. In some cases it may be desirable to remove sugars using endoglycosidases and other enzymes to cleave sugars that interfere with intra- and/or interchain disulfide formation.

KL-CD can be expressed in prokaryotic as well as eukaryotic expression systems. The following are examples of expression vectors which may be used in procaryotic systems:

The pPL expression series use the strong PL promoter of lambda phage, and can be expressed in a number of procaryotic expression systems (Reed, *Cell*, 25, 713–719 (1981), Simatake and Rosenberg, *Nature*, 292, 128–132 (1981), Mott, et al., *Proc. Natl. Acad. Sci. USA*, 82, 88–92 (1985)).

The pOX expression series, which uses the oxygen-dependent promoter of vireoscilia hemoglobin gene, is expressed in *E. coli* (Khosla, et al., *BioTechnology* 8, 554–558 (1990)).

pKK223-3 uses a hybrid promoter derived from the fusion between the promoters of the tryptophan and lactose operons of E. coli (Brosius and Holy, *Proc. Natl. Acad. Sci. USA* 81 6929–6933 (1984)).

The following are examples of expression vectors which may be used for expression in a eukaryotic expression system:

pMSG uses the promoter from the mouse mammary tumor virus long terminal repeat (MMTV). Suitable host cells for pMSG are Chinese hamster ovary cell, Hela cell and mouse Lkt negative cells (Lee, F., et al., *Nature* 294, 28–232 (1981)).

pSVL uses the SV40 late promoter. Suitable host cells are COS cells for high level transient expression (Sprague, et al., *J. Virol.* 45, 773–781 (1983); Gempleton and Eckhart, *Mol. Cell. Biol.* 4, 817–821 (1984)).

pRSV uses Rous Sarcoma Virus promoter. Suitable host cells are mouse fibroblast cells, lymphoblastoid cells and COS cells (Gorman, et al. *Science* 221, 551–553 (1983)).

pBPV is a DNA viral vector derived from bovine papilloma virus. It is stably expressed in mouse mammary tumor cells, C127 (Zin, et al., i Cell 34, 865–879 (1983); Saraver, et al., *Mol. Cell. Biol.* 1, 486–496 (1981)); Saraver, et al.,*Proc. Natl. Acad. Sci., USA* 79, 7147–7151 (1982); Law, et al., *Mol. Cell. Biol.* 3, 2110–2115 (1983)).

Baculovirus expression vectors are stably expressed in insect cells such as Sf9 (Luckow and Summers, *BioTechnology*, 6, 47–55 (1988); Miller, L. K., *Ann. Rev. Microbiology* 42, 177–199 (1988)).

Methods for making transgenic animals are well known. DNA encoding the KL can be introduced into the cells in culture using transfection or into embryos for production of transgenic animals expressing the KLs. As known in the art, transfection can be accomplished by electroporation, calcium phosphate precipitation, a lipofectin-based procedure, or microinjection or through use of a "gene gun". In each case, cDNA encoding the KL is subcloned into a plasmid-based vector which encodes elements for efficient expression in the genetically engineered cell. The plasmid-based vector preferably contains a marker such as the neomycin gene for selection of stable transfectants with the cytotoxic aminoglycoside G418 in eukaryotic cells and an ampicillin gene for plasmid selection in bacteria. In the preferred embodiment, the KL is expressed in soluble form; in the most preferred embodiment, the KL is expressed using a tissue specific protein such as the casein promoter, to avoid potential side effects and to increase recoverable yields.

Infection, which for endothelial cells is preferred, is accomplished by incorporating the genetic sequence for the KL into a retroviral vector. Various procedures are known in the art for such incorporation. One such procedure which has been widely used in the art employs a defective murine retrovirus, Psi-2 cells for packaging the retrovirus, and the amphotropic packaging cell line Psi-AM to prepare infectious amphotropic virus for use in infecting the target donor cells, as described by Kohn et al., 1987 "Retroviral-mediated gene transfer into mammalian cells" *Blood Cells* 13:285–298. Alternatively, rather than a defective Moloney murine retrovirus, a retrovirus of the self-inactivating and double-copy type can be used, such as that described by Hantzopoulos et al., 1989 "Improved gene expression upon transfer of the adenosine deaminase minigene outside the transcriptional unit of a retroviral vector" *Proc. Natl. Acad. Sci. USA* 86:3519–3523.

A variety of methods are known to those skilled in the art for making transgenic animals expressing a KL protein. Examples of particularly useful animals include mice, rats, rabbits, pigs, sheep, and cattle, all of which have been made transgenic using standard techniques. The most well known method for making a transgenic animal is by superovulation of a donor female, surgical removal of the egg and injection of the genetic material in the pronuclei of the embryo, as taught by U.S. Pat. No. 4,873,191 to Wagner, the teachings of which are incorporated herein. Another commonly used technique involves the genetic manipulation of embryonic stem cells (ES cells). ES cells are grown as described, for example, in Robertson, E. J. "Embryo-derived stem cell lines" in: Teratocarcinomas and embryonic stem cells: A practical approach. E. J. Robertson, ed. 71–112 (Oxford-Washington, D.C.: IRL Press, 1987). Genetic material is introduced into the embryonic stem cells, for example, by electroporation according to the method of McMahon, A. P., and Bradley, A. *Cell* 62, 1073–1085 (1991). Colonies are picked from day 6 to day 9 of selection into 96 or 24 well dishes (Costar) and expanded and used to isolate DNA for Southern blot analysis. Chimeric mice are generated as described in Bradley, "Production and analysis of chimaeric mice" in *Teratocarcinomas and embryonic stem cells: A practical approach* E. J. Robertson, ed. pp. 113–151 (Oxford, Washington, D.C. IRL Press 1987), the teachings of which are incorporated herein. Genetic material is injected into blastocysts. From those implanted females that become pregnant, chimaeras are selected from the offspring and bred to produce germline chimaeras for use as donor animals.

Properties of KL-CD

In Example 1, a truncated form of murine KL including amino acids 1 to 164 plus an additional N-terminal methionine required for synthesis in *E. coli* (amino acids 1 to 164 of Sequence ID No. 6) was expressed. This form corresponds to the natural soluble form of murine KL-1. In this method, KL is synthesized and accumulates within the bacteria in an insoluble form. KL-CD is obtained by solubilization of the protein with denaturant (urea), and refolding into biologically active protein by removal of the denaturant (by dialysis into buffer such as Tris™ HCl or PBS). During the refolding, both intrachain and interchain disulfide bonds are formed, resulting in two types of KL which can promote cell proliferation, KL-NC and KL-CD. In addition, a biologically inactive KL-CD is formed. The three forms of KL can be separated from one another and from contaminating *E. coli* proteins using a high resolution chromatography method such as C18 reverse-phase HPLC.

Expression of KL-CD, derived from KL-cDNAs with three cysteines or with greater than four cysteines in eukaryotic cells can be facilitated by expression of the full length KL cDNA (KL-1, Huang, et al., 1992) with the appropriate Cysteine mutation such that KL dimers will associate first in the membrane and then be released via cleavage at the native proteolytic cleavage site.

KL-NC presumably contains the two disulfide bonds normally found in KL. Since the KL-CD forms contain at least one intermolecular disulfide bond, they can have at most, only one of the intramolecular disulfides found in the native molecule. Presumably the biologically active and inactive forms of KL-CD consist of different combinations of intra- and intermolecular disulfide bonds.

Since native KL forms non-covalent dimers in solution, it was of interest to determine the stoichiometry of KL-CD in solution. When KL-CD and KL-NC are co-injected onto an HPLC gel filtration column, the proteins co-elute as a single peak of approximately 40 kDa, suggesting that both KL-CD and KL-NC are dimeric in solution.

Covalent dimers of KL-related proteins

The approaches outlined above for the formation of a covalent dimer of KL may also be applied to the formation of covalent dimers of other non-disulfide linked multimeric proteins. In particular, the recently characterized ligand of the FLT-3/FLK-2 receptor is predicted to be structurally similar to KL based on sequence similarity, and like KL, forms non-covalent dimers in solution. The amino acid sequence of the murine FLT-3 ligand is shown as Sequence ID No. 7, as reported by Lyman, et al., (1993) *Cell* 1157–1167. The full length cDNA can be expressed in eukaryotic cells with vectors specified and soluble protein recovered after proteolytic cleavage via the endogenous protease in CV-1 cells. Alternatively, a soluble form of Flt-3L can be isolated from eukaryotic or prokaryotic cells by expression of a fragment of the cDNA, for example, from amino acid one to 135 or one to 163. Cysteines at positions 119, 124, and 130 can also be replaced by other amino acids, preferably serine. Other modifications such as additional cysteines, in the same region as specified for KL as well as fusion proteins can also be used to produce disulfide linked FLT-3L.

Formation of covalent dimers of the Flt-3 ligand are expected to have desirable biological properties similar to that of KL, including increased potency in stimulating proliferation of bone marrow subpopulations, and increased stability. Biologically active, disulfide-linked covalent dimers of FLT-3L may be obtained more easily with the human form which contains six cysteine residues, rather than with the mouse form, which contains nine cysteines. As with KL, covalent dimers of FLT-3L may be formed by denaturation and refolding, through the addition of cysteines in the region of amino acid 31, via fusion proteins, or by chemical crosslinking means.

Biological Activities and Applications of KL-CD

Native KL has multiple biological activities, affecting the growth and differentiation of a variety of hematopoietic cells, as well as the activation of mast cells. While the mast cell activating property of native KL limits its utility as a therapeutic, KL-CD has properties which make it useful for applications that were originally intended for native KL. As described in Example 3, murine KL-CD is at least ten-fold more potent than murine KL-NC as well as human KL-NC in stimulating the proliferation of two different human cell lines, and ten-fold more potent than murine KL-NC in stimulating the proliferation of murine mast cells. However, KL-CD is only equipotent to that of murine KL-NC in priming mast cells for IgE-dependent degranulation.

The selectivity of KL-CD for promoting cell proliferation but not mast cell degranulation, may make the disulfide-linked form particularly useful as a therapeutic since dosages may be set which promote a desired proliferation event but which avoid mast cell degranulation-induced anaphylaxis. For example, since KL-CD is ten-fold more potent than KL-NC in promoting cell proliferation, a dose of 10 μg/kg/day of KL-CD should be as effective as a 100 μg/kg/day dose of KL-NC, a dose which stimulated significant hematopoietic recovery. Since KL-CD is equipotent to KL-NC in promoting mast cell degranulation, a dose of 10 μg/kg/day of KL-CD is below the dose of 25 μg/kg/day which resulted in mast cell-related side effects in some patients, and well below the dose of KL-NC of 100 μg/kg/day which resulted in serious mast cell-related effects in many patients.

KL-CD can be used to stimulate hematopoietic recovery following chemo/radiotherapy or bone marrow (hematopoietic cell) transplantation, as previously described in the literature, and reviewed in the Background of the Invention. This may be accomplished with KL used as a single agent or in combination with other cytokines, such as G-CSF or GM-CSF for neutrophil recovery, or IL-6 or other factors that promote platelet recovery. KL-CD may also be more effective in treating certain anemias such as those associated with Diamond Blackfan Syndrome, those induced by chemo or radiotherapy or viral infections, or aplastic anemia. The dimer will also be useful in the mobilization of stem cells from the bone marrow to the peripheral blood alone and or in combination with other cytokines, such as G-CSF, or chemotherapy. Since KL-CD would be used at the same dose as KL-NC, which is limited by its toxicity, KL-CD should be significantly more effective than KL-NC in the aforementioned applications, due to its enhanced potency in promoting cell proliferation.

While short-term exposures of mast cells in culture to KL results in mast cell priming, i.e. in enhanced IgE-dependent mast cell degranulation, prolonged exposure of these cells to KL results in a desensitization of the priming effect. This suggests that patients could be desensitized to the mast cell activating effects of KL by treatment with a level of KL-CD below the toxicity level. A subsequent treatment of high level KL-CD or KL-NC might then provide enhanced hematopoietic recovery without causing mast cell associated toxicity. The level of hematopoietic recovery might be greater than that observed for KL-CD used at a level below the toxicity level. In summary, KL-CD or KL-NC should be useful in a desensitization protocol to establish a higher toxicity level for KL.

KL-CD should also have utility for ex vivo applications. Although the differential proliferative/mast cell activating property of KL-CD is less important for ex vivo uses, its increased biological activity make it useful in the culture of hematopoietic cells. KL is effective by itself or preferably in combination with other cytokines, such as IL-1, IL-3, IL-6, IL-11, G-CSF, GM-CSF, LIF, FLT-3L and combinations thereof, for the ex vivo expansion of stem cells and progenitors for transplantation. The ability of KL-CD to stimulate the proliferation of immature stem/progenitor cells makes KL particularly useful in protocols involving the transduction of genes into hematopoietic cells for gene therapy. KL-CD could be used at lower dosages relative to KL-NC for these ex vivo applications. KL-CD might also result in qualitative differences in hematopoietic cell expansion compared to KL-NC, perhaps resulting in the selective expansion of a certain type of progenitor cell.

The greater stability of KL-CD relative to KL-NC may enhance the utility of KL-CD in ex vivo applications. KL-NC exhibits properties in vitro which suggests an inherent instability of the molecule, perhaps due to the dissociation of the dimer into monomers at lower protein concentrations, or to internalization and degradation of the molecule by the responding cells. This is illustrated by repeated daily feeding of mast cell cultures with KL which gives significantly better growth than two to three times a week feeding. It may be possible to use the covalently-linked KL dimer to overcome this apparent instability, and allow one to use a significantly lower concentration of soluble KL-CD to support long term cell cultures.

In summary, KL-CD can be utilized as an additive to cell culture media as extrapolated from the published data relating to KL, or in combination with a pharmaceutically acceptable carrier for administration to a patient. Exemplary pharmaceutical carriers include diluents such as saline and phosphate buffered saline, additives such as preservatives, detergents, solubilizing agents, anti-oxidants, pH buffers, and salts, as well as alternative carrier forms such as polymers, liposomes, micelles, and vesicles. These are administered to a patient in an amount effective to produce an improvement in a particular condition, for example, to increase platelet numbers. Treatment may be alone or in combination with other compounds demonstrated to have hematopoietic activity, including erythropoietin, G-CSF, GM-CSF, interleukins 1–11, IGF-I FLT-3 ligand or LIF.

EXAMPLE 1

Purification and Characterization of Covalent Dimer-Kit Ligand (KL-CD) from Native KL Sequence.

A truncated mouse KL cDNA containing amino acids 1 to 164 (amino acids 1 to 164 of Sequence ID No. 6) was subcloned from the full length cDNA. The endpoint of this truncated cDNA was chosen based on the site of proteolytic cleavage in the native transmembrane form of the molecule which gives rise to the soluble form (Huang et al., 1992). The truncated KL cDNA was cloned into an expression vector, placing it under control of the phage lambda early gene promotor $P_L$. (Lambda II, Hendrix, Roberts, Stahl, Weisberg, editors. Cold Spring Harbor Laboratory, Cold Spring Harbor, N.Y. (1983)). This promoter is regulated in a temperature-sensitive manner by a mutant phage lambda CI gene which is also present on the expression vector. The truncated cDNA was expressed in E. coli strain DH5-a (BRL-GIBCO). As is typical for high level expression in E. coli, the truncated KL accumulated in an insoluble form in inclusion bodies in the bacteria.

A two liter culture of E. coli expressing KL was harvested, the cells were lysed by sonication, and the inclusion bodies containing insoluble KL were isolated by centrifugation at 10,000 ×g. The inclusion bodies were washed by resuspension in 20 mM Tris HC1, pH 7.4 200 mM NaCl 1 mM EDTA and re-centrifuged. The inclusion bodies were solubilized by incubation in 6 M urea at 4° C. for 1 h, followed by centrifugation to remove insoluble material. After solubilization of inclusion bodies containing mKL, the protein was dialyzed against 20 mM Tris pH 8.0 at 4° C. for 48 to 72 h. Insoluble material was removed by centrifugation at 10,000 ×g, and the protein was applied to a Vydak™ C18 1×25 cm HPLC column that had been equilibrated with 0.1 M ammonium acetate pH 6.0 and 25% n-propanol. The column was washed with equilibration buffer, and then eluted with a linear gradient from 30–50% n-propanol, 0.1 M ammonium acetate pH 6.0.

mKL bioactivity, as measured by the ability to promote proliferation of the cell line MO7e described in Example 2, elutes in two peaks; non-covalently linked mKL (KL-NC)

elutes at approximately 38% n-propanol, KL-CD elutes at approximately 45% n-propanol, as shown in FIG. 2A. A third peak containing a different form of KL-CD with very low activity elutes after the biologically active KL-CD peak, as also shown in FIG. 2A.

The KL-NC and KL-CD peaks were purified to homogeneity by re-application to the C18 column, and elution with narrower gradients. KL-NC was purified using a gradient from 32–45% n-propanol. The active and inactive KL-CD forms were purified using a 2 h gradient of 35–45% n-propanol. After the second C18 column, the NC and CD forms were in a highly purified state, and contained low levels of *E. coli* -derived endotoxin (less than 1 E.U. per mg protein as assayed by the BioWhittaker Inc. Amebocyte Lysate Assay). Prepared through these means, approximately 15% of the mKL refolds into active KL-CD, 15% into inactive KL-CD, and 70% into KL-NC.

Figure 2B:
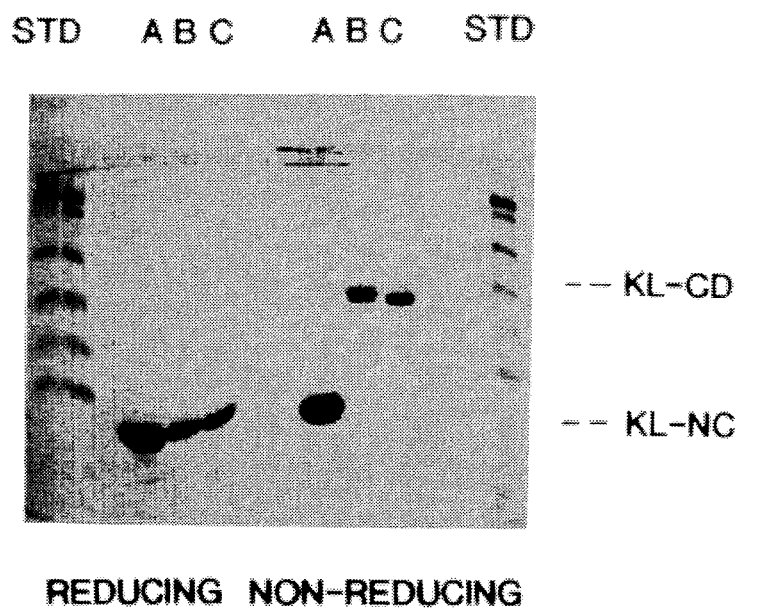
FIG. 2B is a photograph of SDS PAGE under reducing and non-reducing conditions of KL-CD and KL-NC eluted from the C18 column shown in FIG. 2A.
Figure 2C:
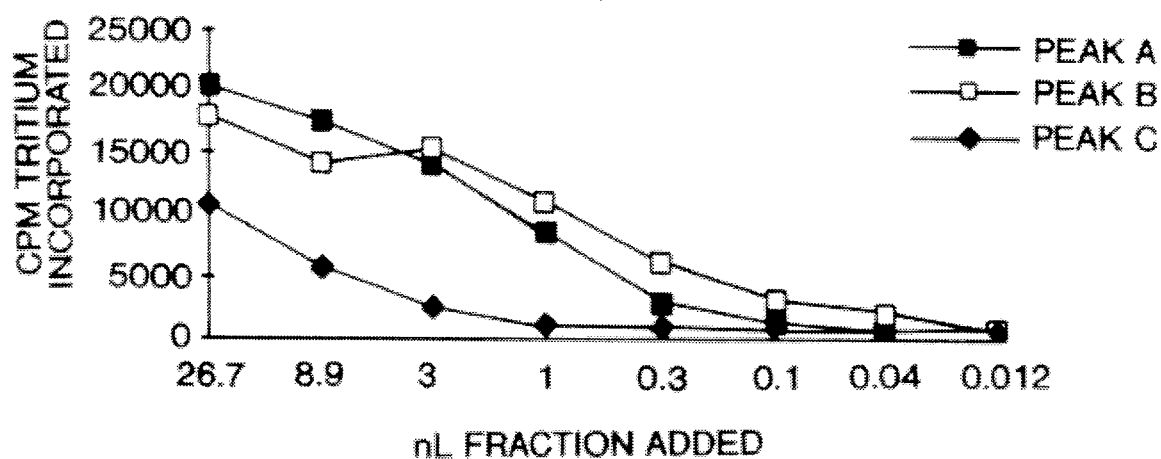
FIG. 2C is a graph of KL bioactivity, CPM tritium incorporated versus nL fraction shown in FIG. 2A added, for peak A (dark squares), peak B (open squares), and peak C (dark diamonds) of FIG. 2A, as measured by the ability to promote proliferation of the cell line MO7e.

The difference between KL-NC and the two KL-CD forms can be seen not only by their different retention times on the C18 column, but by SDS-PAGE under reducing/non-reducing conditions, as shown in FIG. 2B. Under reduced conditions, KL-NC as well as the two forms of KL-CD migrate with an apparent molecular weight of about 18 kDa. Under non-reduced conditions, KL-NC migrates with an apparent molecular weight of about 18 kDa, while the two different forms of KL-CD migrate with an apparent molecular weight of 36 kDa. As assessed by SDS-PAGE under non-reducing conditions, the active form of KL-CD has a slightly greater apparent molecular weight than the inactive form of KL-CD. The higher apparent molecular weight of KL-CD as compared with KL-NC under non-reducing conditions is indicative of the covalent linkage of two KL monomers via at least one disulfide bond.

The nature of KL-CD and KL-NC has been confirmed by Laser Desorption/Time of Flight Mass Spectrometry. By this method, KL-NC has a mass of 18,440 daltons. Both active and inactive KL-CD had a mass of 36,860 daltons; these forms apparently differ only in their disulfide bonds, with inactive KL-CD containing a disulfide bond arrangement which greatly diminishes activity.

EXAMPLE 2

Formation of KL-CD from KL-NC via disulfide rearrangement.

KL-CD can also be derived from pure KL-NC through a non-enzymatic reaction involving the rearrangement of disulfide bonds. The reaction consists of pure, correctly folded KL-NC at 1 mg/ml, 50 mM Tris pH 9.0, 2 M guanidine-HCl (added to partially unfold the KL-NC), and reduced and oxidized forms of glutathione (500 μM and 125 μM final concentration, respectively). The reaction mixture was incubated for 20 h at 22° C., and then dialyzed against 0.1 M ammonium acetate at 4° C. to remove the guanidine to allow folding and to stop disulfide exchange. The rearrangement reaction was monitored by SDS-PAGE under non-reducing conditions.

Proteins with molecular weights of the active and inactive forms of KL-CD were formed via rearrangement of KL-NC disulfides. This rearrangement required the presence of 2 M guanidine-HCl. Additionally, several other KL species were formed, which might be inactive forms of KL-CD. The mixture of proteins resulting from disulfide rearrangement of KL-NC was purified by C18 reverse phase chromatography as in Example 1.

Figure 3A:
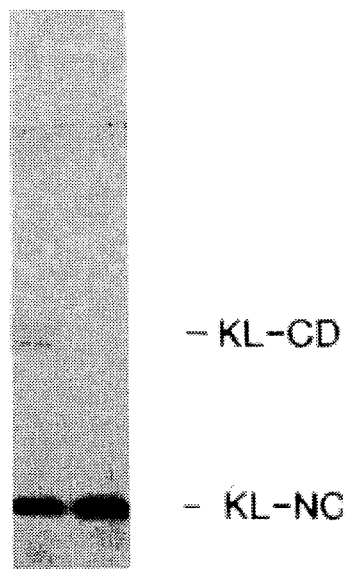
FIG. 3A is a photograph of SDS-PAGE of KL-CD and KL-NC refolded from KL-NC in the presence or absence of glutathione.
Figure 3B:
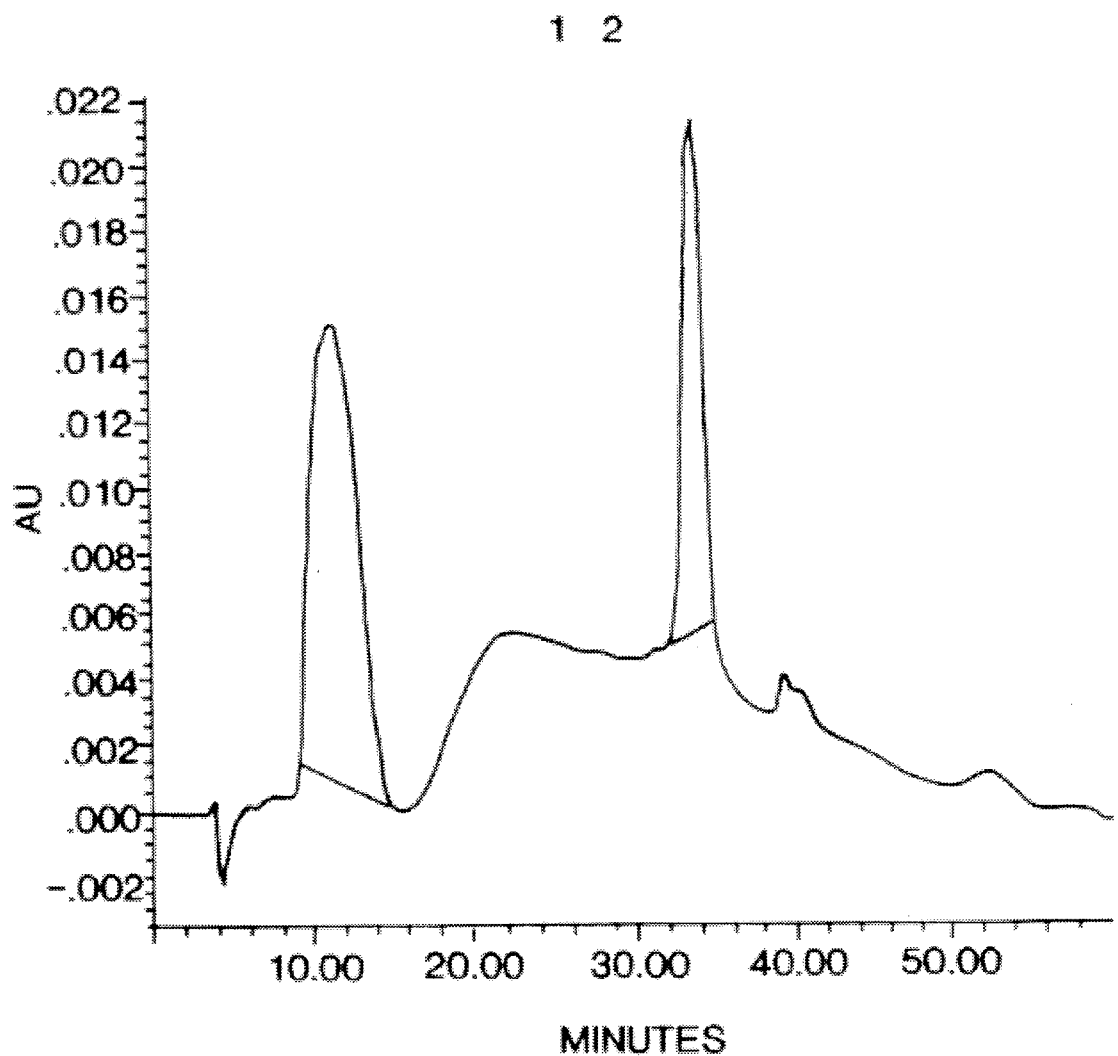
FIG. 3B is a chromatogram of a C18 reverse phase HPLC separation of refolded material as shown in FIG. 3A.
Figure 3C:
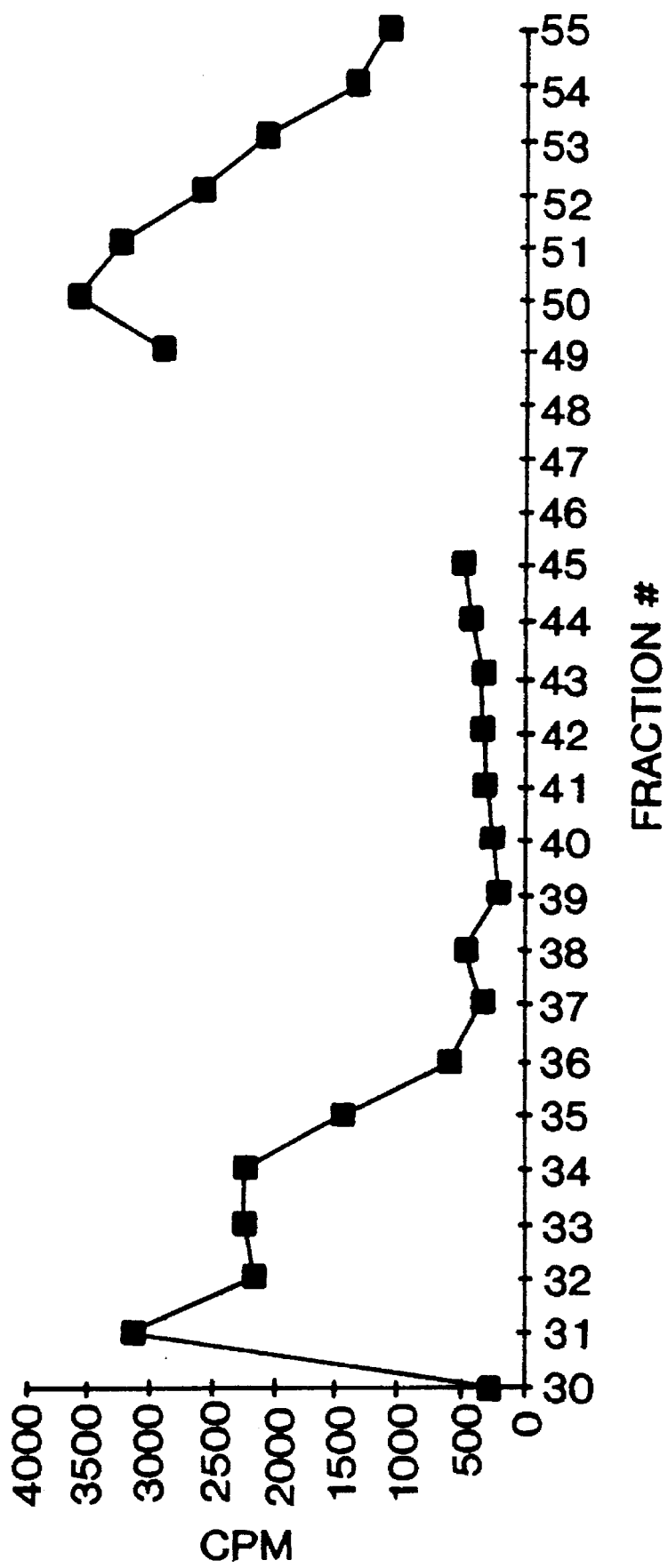
FIG. 3C is a graph of KL bioactivity of fraction from the chromatogram shown in FIG. 3*b*.

FIG. 3A is a photograph of SDS-PAGE of KL-CD and KL-NC refolded from KL-NC in the presence or absence of glutathione. FIG. 3B is a chromatogram of a C18 reverse phase HPLC separation of refolded material as shown in FIG. 3A. FIG. 3C is a graph of KL bioactivity of fractions from the chromatogram shown in FIG. 3b.

Figure 4:
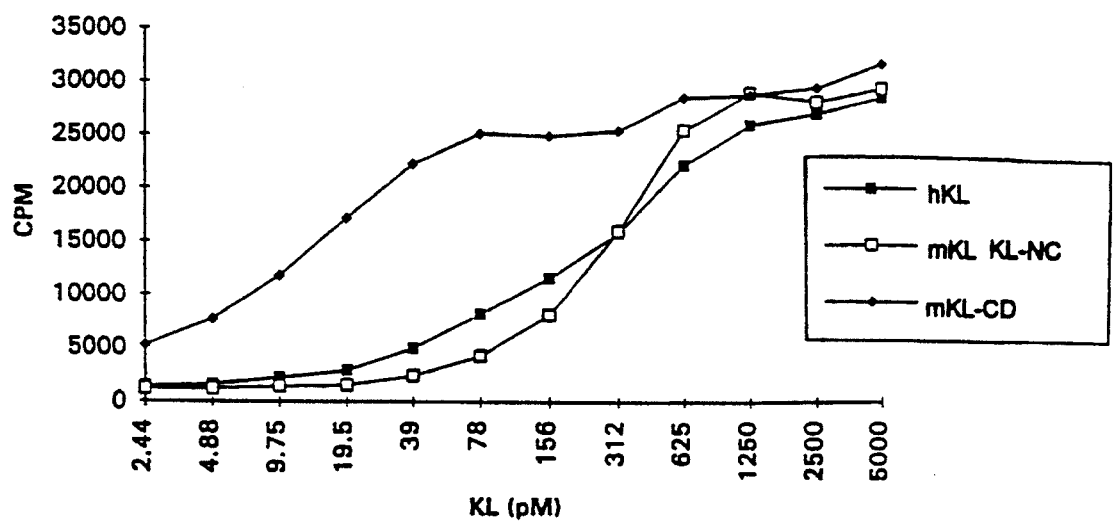
FIG. 4 is a graph of KL bioactivity showing proliferation of MO7e in response to purified KL-NC (open squares), KL-CD (dark diamonds), and human KL (dark squares).

Two peaks of biologically active KL were identified; the second peak consisted of KL-CD which migrates with the same apparent molecular weight of KL-CD purified as in Example 1 in SDS-PAGE under reducing conditions. Although much greater amounts of KL-NC were present after disulfide rearrangement, C18 fractions containing KL-NC or KL-CD had comparable activity in promoting cell proliferation, as shown by FIG. 4. This shows that KL-CD with increased biological activity can be formed from KL-NC through disulfide rearrangement.

Disulfide rearrangement conditions can be established which maximize KL-CD formation. It may be preferable however to purify recombinant KL in a completely unfolded state by C18 reverse-phase HPLC, and then fold the protein into CD- and NC- KL forms using the disulfide-rearrangement conditions described above.

EXAMPLE 3

Biological activity of KL-CD in in vitro biological assays.
  a. Cell proliferation.

KL supports the proliferation of a variety of growth factor dependent cell lines. Murine KL is equally potent on both human and murine cells, while human KL is active on human cells but shows minimal activity on murine cells. The human megakaryocytic cell line M07e, which is maintained in the presence of GM-CSF, is used to assess human and murine KL. Murine bone marrow-derived mast cells (BMMC), which are established and then maintained for up to three months in the presence of IL-3 (Yung, Y. P., et al. (1982) *J. Immunol.*, 129, 1256–1261), are also used to assess the activity of murine KL (Nocka, K., et al. (1990).

The cells are washed and resuspended in media lacking their maintenance growth factor and plated into 96 well plates. Column fractions of KL samples are added and serially diluted and the cells are incubated at 37° C. for 24 h. The cells are then pulsed with 2.5 μCi/ml of $[^3]$H-Thymidine for 6–12 hr, harvested onto glass fiber filters, and the amount of $^3$H-thymidine on the filter is determined on a Packard TopCount™ scintillation counter. The data is analyzed by plotting the CPM $^3$H incorporated into DNA versus the concentration of KL.

b. Mast Cell Priming Activity

Figure 5:
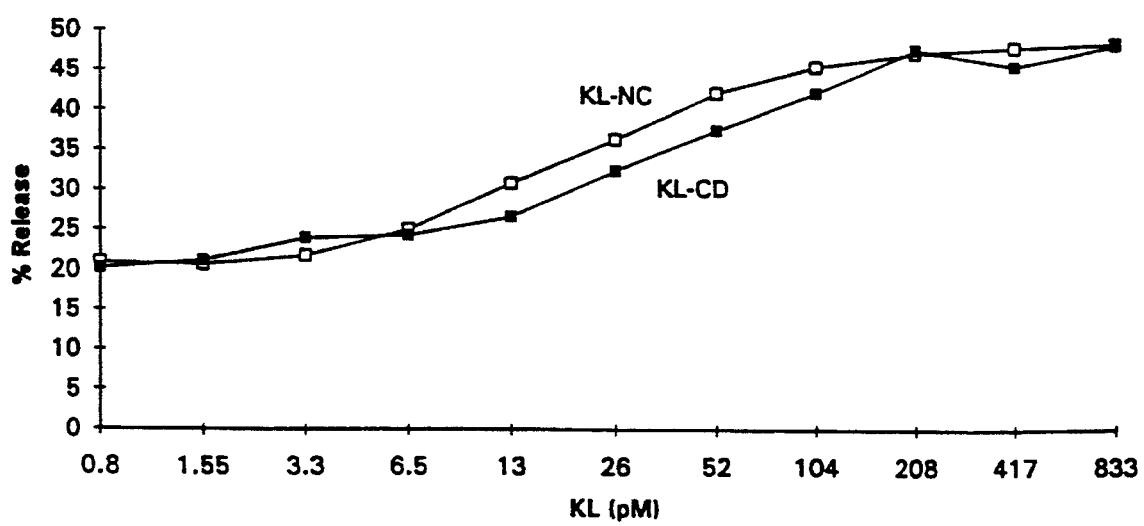
FIG. 5 is a graph of mast cell activation (% release) by purified KL-NC (open squares) and KL-CD (dark squares) in the presence of anti-TNP and TNP-BSA.

Primary cultures of murine mast cells derived from bone marrow and cultured in IL-3 (BMMC) can be utilized not only for proliferation assays as described above, but may also be used as a quantitative and sensitive measure of the priming or activation potential of cytokines. With human mast cells, KL is the most potent cytokine identified to date with significant mast cell priming activity in vitro (Bischoff and Dahinden (1992) *J. Exp. Med.*, 175, 237–244). Murine BMMC sensitized with IgE immunoreactive with trinitrophenol (TNP) (ascites from IGELa2, ATCC # TIB 142) can be primed by KL such that when stimulated with specific antigen (TNP-BSA), exhibit a significant increase in the release of mediators compared to unprimed cells. When BMMC derived from the C57/B16×DBA2 F1 (BDF1) strain of mice are activated at low cell density ($1\times10^5$ cells/ml) in physiological buffer, low levels of proinflammatory mediators and secretory granule enzymes, typically 10–25% of their granule hexosaminidase, are released upon stimulation with IgE and antigen alone. Following a short priming period with KL (0 to 10 minutes), maximal granule enzyme release in the range of 40 to 60% enzyme release is observed. FIG. 5 is a graph of mast cell activation by purified KL-NC and KL-CD as a function of concentration. The mast cell priming activity of native KL has an $ED_{50}$ of 0.5 to 1 ng/ml in this assay.

EXAMPLE 4

Desensitization of mast cells to a KL response.

Human lung and murine bone marrow derived mast cells respond to the exposure of various priming agents with very rapid kinetics, as described by Bischoff and Dahinden (1992). The priming assay as specified in Example 3 is typically carried out with a priming period of 5 to 10 minutes followed by the addition of antigen for a further period of 10 minutes. As shown below, if the antigen is withheld for 30 minutes or longer, the priming affect of KL is lost and the level of degranulation is similar to that seen with antigen alone. Furthermore, BMMCs can no longer respond to a second treatment with KL when they have already been desensitized. Once the effect of Kl is lost, mast cells cannot respond to a second dose of KL within a one to two hour period. This desensitization could be used therefore to minimize a response to a subsequent therapeutic dose of KL.

Kinetics of Priming with KL

BMMCs which had been previously sensitized with IgE (anti-TNP) were incubated with control diluent or KL for various periods of time (0, 2, 5, 7, 10, 20, 30, 40, 50, and 60 minutes) and then activated with antigen (TNP-BSA). Percent release of hexoseaminidase was determined ten minutes after the addition of antigen.

Figure 6:
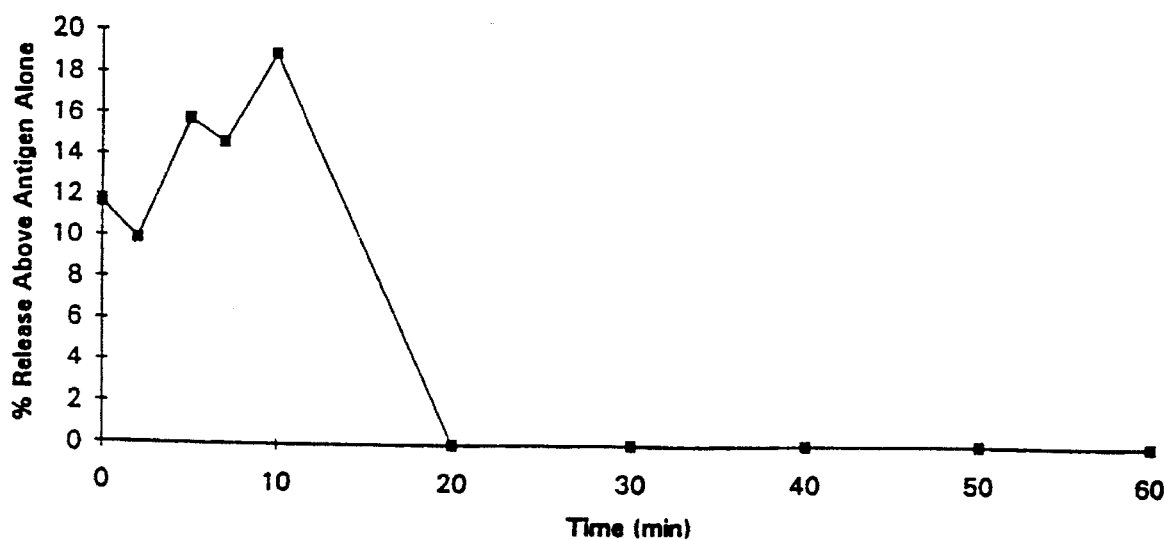
FIG. 6 is a graph of enhancement of mast cell degranulation (percent release above antigen alone) versus time (minutes) for KL.

Exposure of cells to KL for up to ten minutes prior to antigen resulted in maximal activation, as shown by FIG. 6. With exposure of cells to KL for 20 minutes and longer, no significant release was observed above that seen with antigen alone.

Desensitization of mast cells with KL

Figure 7:
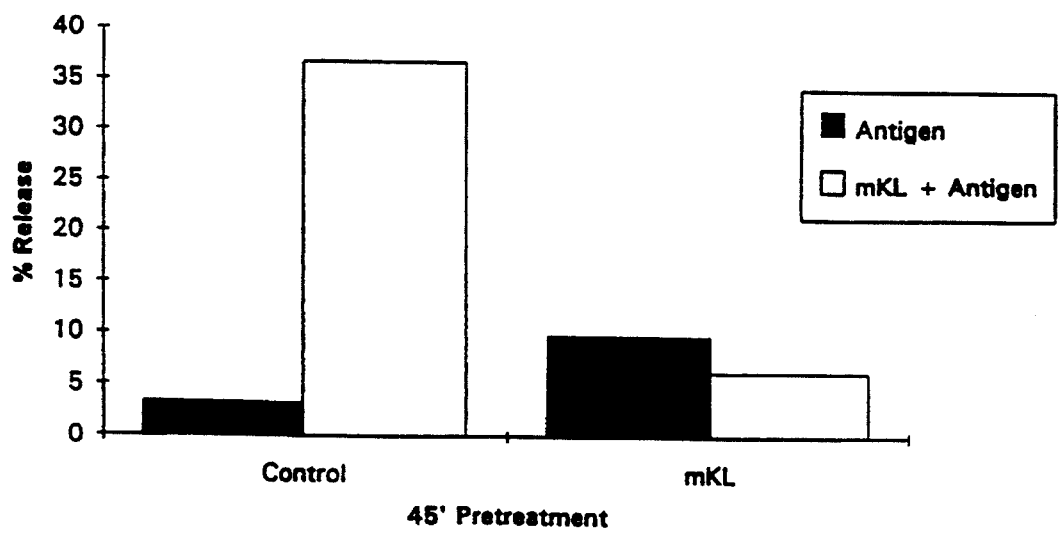
FIG. 7 is a bar graph of the desensitization of mast cell degranulation using antigen (dark bars) alone or after prior exposure to KL (open bars).

Sensitized BMMCs were incubated in the presence or absence of KL for 45 minutes (1st phase). Following this incubation period, cells were washed and BMMCs were primed with either control diluent, or KL for 10 minutes (2nd phase). Cells were then activated by the addition of antigen for a further 10 minutes. Cells that had been cultured in the control medium for the 45 minute period responded to antigen and exhibited a significant enhancement when treated with KL as the second agent and then antigen. However, cells that had been pretreated with KL were only activated to the level seen with antigen alone. Secondary stimulation with KL did not lead to enhanced degranulation, as shown by FIG. 7.

Modifications and variations of the present invention will be obvious to those skilled in the art from the foregoing detailed description. Such modifications and variations are intended to come within the scope of the appended claims.

---

We claim:

1. A biologically active, interchain disulfide-linked dimer of kit ligand consisting of two monomers, each of said monomers having the same amino acid sequence and comprising at least amino acids 1 to 138 of a kit ligand amino acid sequence, said dimer being essentially free of said monomers and inactive dimers of kit ligand.

2. The dimer of claim 1 wherein the kit ligand amino acid sequence in the monomers is selected from the group consisting of kit ligand amino acids 1–138, kit ligand amino acids 1–162, kit ligand amino acids 1–164, and kit ligand amino acids 1–165.

3. The dimer of claim 1 additionally having intrachain disulfide bonds.

4. A method for making a kit ligand dimer according to any one of claims 1, 2 or 3, wherein said dimer displays enhanced proliferating activity relative to mast cell activating activity as compared with wild type activity, comprising the steps of:

a) denaturing a monomer comprising at least amino acids 1 to 138 of a kit ligand amino acid sequence under conditions that cause reduction of disulfide bonds;

b) denaturing said denatured monomer under conditions that allow the formation of biologically active, interchain disulfide-linked covalent kit ligand dimers; and c) separating said biologically active covalent kit ligand dimers from inactive covalent kit ligand dimers and said monomers.

5. The method of claim 4 wherein the denaturant is 6M urea or 2M quanidine-HCl, and renaturation is achieved by dialyzing under physiological conditions.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 838 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 17..835

( i x ) FEATURE:
        ( A ) NAME/KEY: sig_peptide
        ( B ) LOCATION: 17..91

( i x ) FEATURE:
        ( A ) NAME/KEY: mat_peptide
        ( B ) LOCATION: 92..835

( x ) PUBLICATION INFORMATION:
        ( A ) AUTHORS: Martin, et al.
        ( C ) JOURNAL: Cell
        ( D ) VOLUME: 63
        ( F ) PAGES: 203-211
        ( G ) DATE: 1990
        ( K ) RELEVANT RESIDUES IN SEQ ID NO:1: FROM 1 TO 273

( x i ) SEQUENCE DESCRIPTION: SEQ ID NO:1:

AGCGCTGCCT TTCCTT ATG AAG AAG ACA CAA ACT TGG ATT CTC ACT TGC    49

```
                Met  Lys  Lys  Thr  Gln  Thr  Trp  Ile  Leu  Thr  Cys
                -25                 -20                      -15
ATT  TAT  CTT  CAG  CTG  CTC  CTA  TTT  AAT  CCT  CTC  GTC  AAA  ACT  GAA  GGG         97
Ile  Tyr  Leu  Gln  Leu  Leu  Leu  Phe  Asn  Pro  Leu  Val  Lys  Thr  Glu  Gly
          -10                      -5                             1

ATC  TGC  AGG  AAT  CGT  GTG  ACT  AAT  AAT  GTA  AAA  GAC  GTC  ACT  AAA  TTG        145
Ile  Cys  Arg  Asn  Arg  Val  Thr  Asn  Asn  Val  Lys  Asp  Val  Thr  Lys  Leu
               5                        10                   15

GTG  GCA  AAT  CTT  CCA  AAA  GAC  TAC  ATG  ATA  ACC  CTC  AAA  TAT  GTC  CCC        193
Val  Ala  Asn  Leu  Pro  Lys  Asp  Tyr  Met  Ile  Thr  Leu  Lys  Tyr  Val  Pro
          20                   25                        30

GGG  ATG  GAT  GTT  TTG  CCA  AGT  CAT  TGT  TGG  ATA  AGC  GAG  ATG  GTA  GTA        241
Gly  Met  Asp  Val  Leu  Pro  Ser  His  Cys  Trp  Ile  Ser  Glu  Met  Val  Val
35                        40                        45                        50

CAA  TTG  TCA  GAC  AGC  TTG  ACT  GAT  CTT  CTG  GAC  AAG  TTT  TCA  AAT  ATT        289
Gln  Leu  Ser  Asp  Ser  Leu  Thr  Asp  Leu  Leu  Asp  Lys  Phe  Ser  Asn  Ile
                    55                        60                        65

TCT  GAA  GGC  TTG  AGT  AAT  TAT  TCC  ATC  ATA  GAC  AAA  CTT  GTG  AAT  ATA        337
Ser  Glu  Gly  Leu  Ser  Asn  Tyr  Ser  Ile  Ile  Asp  Lys  Leu  Val  Asn  Ile
               70                        75                        80

GTG  GAT  GAC  CTT  GTG  GAG  TGC  GTG  AAA  GAA  AAC  TCA  TCT  AAG  GAT  CTA        385
Val  Asp  Asp  Leu  Val  Glu  Cys  Val  Lys  Glu  Asn  Ser  Ser  Lys  Asp  Leu
          85                        90                        95

AAA  AAA  TCA  TTC  AAG  AGC  CCA  GAA  CCC  AGG  CTC  TTT  ACT  CCT  GAA  GAA        433
Lys  Lys  Ser  Phe  Lys  Ser  Pro  Glu  Pro  Arg  Leu  Phe  Thr  Pro  Glu  Glu
100                      105                      110

TTC  TTT  AGA  ATT  TTT  AAT  AGA  TCC  ATT  GAT  GCC  TTC  AAG  GAC  TTT  GTA        481
Phe  Phe  Arg  Ile  Phe  Asn  Arg  Ser  Ile  Asp  Ala  Phe  Lys  Asp  Phe  Val
115                      120                      125                      130

GTG  GCA  TCT  GAA  ACT  AGT  GAT  TGT  GTG  GTT  TCT  TCA  ACA  TTA  AGT  CCT        529
Val  Ala  Ser  Glu  Thr  Ser  Asp  Cys  Val  Val  Ser  Ser  Thr  Leu  Ser  Pro
                    135                      140                      145

GAG  AAA  GAT  TCC  AGA  GTC  AGT  GTC  ACA  AAA  CCA  TTT  ATG  TTA  CCC  CCT        577
Glu  Lys  Asp  Ser  Arg  Val  Ser  Val  Thr  Lys  Pro  Phe  Met  Leu  Pro  Pro
               150                      155                      160

GTT  GCA  GCC  AGC  TCC  CTT  AGG  AAT  GAC  AGC  AGT  AGC  AGT  AAT  AGG  AAG        625
Val  Ala  Ala  Ser  Ser  Leu  Arg  Asn  Asp  Ser  Ser  Ser  Ser  Asn  Arg  Lys
          165                      170                      175

GCC  AAA  AAT  CCC  CCT  GGA  GAC  TCC  AGC  CTA  CAC  TGG  GCA  GCC  ATG  GCA        673
Ala  Lys  Asn  Pro  Pro  Gly  Asp  Ser  Ser  Leu  His  Trp  Ala  Ala  Met  Ala
     180                      185                      190

TTG  CCA  GCA  TTG  TTT  TCT  CTT  ATA  ATT  GGC  TTT  GCT  TTT  GGA  GCC  TTA        721
Leu  Pro  Ala  Leu  Phe  Ser  Leu  Ile  Ile  Gly  Phe  Ala  Phe  Gly  Ala  Leu
195                      200                      205                      210

TAC  TGG  AAG  AAG  AGA  CAG  CCA  AGT  CTT  ACA  AGG  GCA  GTT  GAA  AAT  ATA        769
Tyr  Trp  Lys  Lys  Arg  Gln  Pro  Ser  Leu  Thr  Arg  Ala  Val  Glu  Asn  Ile
               215                      220                      225

CAA  ATT  AAT  GAA  GAG  GAT  AAT  GAG  ATA  AGT  ATG  TTG  CAA  GAG  AAA  GAG        817
Gln  Ile  Asn  Glu  Glu  Asp  Asn  Glu  Ile  Ser  Met  Leu  Gln  Glu  Lys  Glu
               230                      235                      240

AGA  GAG  TTT  CAA  GAA  GTG  TAA                                                     838
Arg  Glu  Phe  Gln  Glu  Val
245
```

( 2 ) INFORMATION FOR SEQ ID NO:2:

( i ) SEQUENCE CHARACTERISTICS:
        ( A ) LENGTH: 273 amino acids
        ( B ) TYPE: amino acid
        ( D ) TOPOLOGY: linear ( i i ) MOLECULE TYPE: protein ( i x ) FEATURE:
  ( A ) NAME/KEY: cleavage site
  ( B ) LOCATION: 164..165

( x i ) SEQUENCE DESCRIPTION: SEQ ID NO:2:

```
Met   Lys   Lys   Thr   Gln   Thr   Trp   Ile   Leu   Thr   Cys   Ile   Tyr   Leu   Gln   Leu
-25               -20                           -15                           -10

Leu   Leu   Phe   Asn   Pro   Leu   Val   Lys   Thr   Glu   Gly   Ile   Cys   Arg   Asn   Arg
                  -5                             1                             5

Val   Thr   Asn   Asn   Val   Lys   Asp   Val   Thr   Lys   Leu   Val   Ala   Asn   Leu   Pro
            10                      15                            20

Lys   Asp   Tyr   Met   Ile   Thr   Leu   Lys   Tyr   Val   Pro   Gly   Met   Asp   Val   Leu
            25                      30                            35

Pro   Ser   His   Cys   Trp   Ile   Ser   Glu   Met   Val   Val   Gln   Leu   Ser   Asp   Ser
40                            45                            50                            55

Leu   Thr   Asp   Leu   Leu   Asp   Lys   Phe   Ser   Asn   Ile   Ser   Glu   Gly   Leu   Ser
                        60                            65                            70

Asn   Tyr   Ser   Ile   Ile   Asp   Lys   Leu   Val   Asn   Ile   Val   Asp   Asp   Leu   Val
                  75                            80                            85

Glu   Cys   Val   Lys   Glu   Asn   Ser   Ser   Lys   Asp   Leu   Lys   Lys   Ser   Phe   Lys
            90                            95                            100

Ser   Pro   Glu   Pro   Arg   Leu   Phe   Thr   Pro   Glu   Glu   Phe   Phe   Arg   Ile   Phe
105                           110                           115

Asn   Arg   Ser   Ile   Asp   Ala   Phe   Lys   Asp   Phe   Val   Val   Ala   Ser   Glu   Thr
120                           125                           130                           135

Ser   Asp   Cys   Val   Val   Ser   Ser   Thr   Leu   Ser   Pro   Glu   Lys   Asp   Ser   Arg
                        140                           145                           150

Val   Ser   Val   Thr   Lys   Pro   Phe   Met   Leu   Pro   Pro   Val   Ala   Ala   Ser   Ser
                  155                           160                           165

Leu   Arg   Asn   Asp   Ser   Ser   Ser   Asn   Arg   Lys   Ala   Lys   Asn   Pro   Pro
                  170                           175                           180

Gly   Asp   Ser   Ser   Leu   His   Trp   Ala   Ala   Met   Ala   Leu   Pro   Ala   Leu   Phe
            185                           190                           195

Ser   Leu   Ile   Ile   Gly   Phe   Ala   Phe   Gly   Ala   Leu   Tyr   Trp   Lys   Lys   Arg
200                           205                           210                           215

Gln   Pro   Ser   Leu   Thr   Arg   Ala   Val   Glu   Asn   Ile   Gln   Ile   Asn   Glu   Glu
                        220                           225                           230

Asp   Asn   Glu   Ile   Ser   Met   Leu   Gln   Glu   Lys   Glu   Arg   Glu   Phe   Gln   Glu
                  235                           240                           245

Val
```

( 2 ) INFORMATION FOR SEQ ID NO:3:

( i ) SEQUENCE CHARACTERISTICS:
    ( A ) LENGTH: 630 base pairs
    ( B ) TYPE: nucleic acid
    ( C ) STRANDEDNESS: double
    ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: CDS
    ( B ) LOCATION: 26..628

( i x ) FEATURE:

( A ) NAME/KEY: sig_peptide
( B ) LOCATION: 26..100

( i x ) FEATURE:
( A ) NAME/KEY: mat_peptide
( B ) LOCATION: 101..628

( x ) PUBLICATION INFORMATION:
( H ) DOCUMENT NUMBER: WO 91/05795 A1
( I ) FILING DATE: 28-SEP-1990
( J ) PUBLICATION DATE: 02-MAY-1991
( K ) RELEVANT RESIDUES IN SEQ ID NO:3: FROM 1 TO 630

( x i ) SEQUENCE DESCRIPTION: SEQ ID NO:3:

| | | | | | | | | | | | | | | | |
|---|---|---|---|---|---|---|---|---|---|---|---|---|---|---|---|
| CTGGATCGCA | GCGCTGCCTT | TCCTT | ATG | AAG | AAG | ACA | CAA | ACT | TGG | ATT | ATC | | | | 52 |
| | | | Met | Lys | Lys | Thr | Gln | Thr | Trp | Ile | Ile | | | | |
| | | | -25 | | | | | -20 | | | | | | | |
| ACT | TGC | ATT | TAT | CTT | CAA | CTG | CTC | CTA | TTT | AAT | CCT | CTC | GTC | AAA | ACT | 100 |
| Thr | Cys | Ile | Tyr | Leu | Gln | Leu | Leu | Leu | Phe | Asn | Pro | Leu | Val | Lys | Thr |
| | -15 | | | | -10 | | | | | -5 | | | | | |
| CAG | GAG | ATC | TGC | AGG | AAT | CCT | GTG | ACT | GAT | AAT | GTA | AAA | GAC | ATT | ACA | 148 |
| Gln | Glu | Ile | Cys | Arg | Asn | Pro | Val | Thr | Asp | Asn | Val | Lys | Asp | Ile | Thr |
| 1 | | | | 5 | | | | | 10 | | | | | 15 | |
| AAA | CTG | GTG | GCG | AAT | CTT | CCA | AAT | GAC | TAT | ATG | ATA | ACC | CTC | AAC | TAT | 196 |
| Lys | Leu | Val | Ala | Asn | Leu | Pro | Asn | Asp | Tyr | Met | Ile | Thr | Leu | Asn | Tyr |
| | | | 20 | | | | | 25 | | | | | 30 | | |
| GTC | GCC | GGG | ATG | GAT | GTT | TTG | CCT | AGT | CAT | TGT | TGG | TTA | CGA | GAT | ATG | 244 |
| Val | Ala | Gly | Met | Asp | Val | Leu | Pro | Ser | His | Cys | Trp | Leu | Arg | Asp | Met |
| | | 35 | | | | | 40 | | | | | 45 | | | |
| GTA | ACA | CAC | TTA | TCA | GTC | AGC | TTG | ACT | ACT | CTT | CTG | GAC | AAG | TTT | TCA | 292 |
| Val | Thr | His | Leu | Ser | Val | Ser | Leu | Thr | Thr | Leu | Leu | Asp | Lys | Phe | Ser |
| | 50 | | | | | 55 | | | | | 60 | | | | |
| AAT | ATT | TCT | GAA | GGC | TTG | AGT | AAT | TAT | TCC | ATC | ATA | GAC | AAA | CTT | GGG | 340 |
| Asn | Ile | Ser | Glu | Gly | Leu | Ser | Asn | Tyr | Ser | Ile | Ile | Asp | Lys | Leu | Gly |
| 65 | | | | | 70 | | | | | 75 | | | | | 80 |
| AAA | ATA | GTG | GAT | GAC | CTC | GTG | GCA | TGT | ATG | GAA | GAA | AAT | GCA | CCT | AAG | 388 |
| Lys | Ile | Val | Asp | Asp | Leu | Val | Ala | Cys | Met | Glu | Glu | Asn | Ala | Pro | Lys |
| | | | | 85 | | | | | 90 | | | | | 95 | |
| AAT | GTA | AAA | GAA | TCA | CTG | AAG | AAG | CCA | GAA | ACT | AGA | AAC | TTT | ACT | CCT | 436 |
| Asn | Val | Lys | Glu | Ser | Leu | Lys | Lys | Pro | Glu | Thr | Arg | Asn | Phe | Thr | Pro |
| | | | 100 | | | | | 105 | | | | | 110 | | |
| GAA | GAA | TTC | TTT | AGT | ATT | TTC | AAT | AGA | TCC | ATT | GAT | GCC | TTC | AAG | GAC | 484 |
| Glu | Glu | Phe | Phe | Ser | Ile | Phe | Asn | Arg | Ser | Ile | Asp | Ala | Phe | Lys | Asp |
| | | 115 | | | | | 120 | | | | | 125 | | | |
| TTC | ATG | GTG | GCA | TCT | GAC | ACT | AGT | GAT | TGT | GTG | CTC | TCT | TCA | ACA | TTA | 532 |
| Phe | Met | Val | Ala | Ser | Asp | Thr | Ser | Asp | Cys | Val | Leu | Ser | Ser | Thr | Leu |
| | 130 | | | | | 135 | | | | | 140 | | | | |
| GGT | CCT | GAG | AAA | GAT | TCC | AGA | GTC | AGT | GTC | ACA | AAA | CCA | TTT | ATG | TTA | 580 |
| Gly | Pro | Glu | Lys | Asp | Ser | Arg | Val | Ser | Val | Thr | Lys | Pro | Phe | Met | Leu |
| 145 | | | | | 150 | | | | | 155 | | | | | 160 |
| CCC | CCT | GTT | GCA | GCC | AGT | TCC | CTT | AGG | AAT | GAC | AGC | AGT | AGC | AGT | AAT | 628 |
| Pro | Pro | Val | Ala | Ala | Ser | Ser | Leu | Arg | Asn | Asp | Ser | Ser | Ser | Ser | Asn |
| | | | | 165 | | | | | 170 | | | | | 175 | |
| AG | | | | | | | | | | | | | | | | 630 |

( 2 ) INFORMATION FOR SEQ ID NO:4:

( i ) SEQUENCE CHARACTERISTICS:
( A ) LENGTH: 201 amino acids
( B ) TYPE: amino acid
( D ) TOPOLOGY: linear ( i i ) MOLECULE TYPE: protein ( i x ) FEATURE:

( A ) NAME/KEY: cleavage site
        ( B ) LOCATION: 164..165

( x i ) SEQUENCE DESCRIPTION: SEQ ID NO:4:

| Met<br>-25 | Lys | Lys | Thr | Gln<br>-20 | Thr | Trp | Ile | Ile | Cys<br>-15 | Ile | Tyr | Leu | Gln | Leu<br>-10 |
|---|---|---|---|---|---|---|---|---|---|---|---|---|---|---|
| Leu | Leu | Phe | Asn | Pro<br>-5 | Leu | Val | Lys | Thr | Gln | Glu<br>1 | Ile | Cys | Arg<br>5 | Asn | Pro |
| Val | Thr | Asp<br>10 | Asn | Val | Lys | Asp | Ile<br>15 | Thr | Lys | Leu | Val | Ala<br>20 | Asn | Leu | Pro |
| Asn | Asp<br>25 | Tyr | Met | Ile | Thr | Leu<br>30 | Asn | Tyr | Val | Ala | Gly<br>35 | Met | Asp | Val | Leu |
| Pro<br>40 | Ser | His | Cys | Trp | Leu<br>45 | Arg | Asp | Met | Val | Thr<br>50 | His | Leu | Ser | Val | Ser<br>55 |
| Leu | Thr | Thr | Leu | Leu<br>60 | Asp | Lys | Phe | Ser | Asn<br>65 | Ile | Ser | Glu | Gly | Leu<br>70 | Ser |
| Asn | Tyr | Ser | Ile<br>75 | Ile | Asp | Lys | Leu | Gly<br>80 | Lys | Ile | Val | Asp | Asp<br>85 | Leu | Val |
| Ala | Cys | Met<br>90 | Glu | Glu | Asn | Ala | Pro<br>95 | Lys | Asn | Val | Lys | Glu<br>100 | Ser | Leu | Lys |
| Lys | Pro<br>105 | Glu | Thr | Arg | Asn | Phe<br>110 | Thr | Pro | Glu | Glu | Phe<br>115 | Phe | Ser | Ile | Phe |
| Asn<br>120 | Arg | Ser | Ile | Asp | Ala<br>125 | Phe | Lys | Asp | Phe | Met<br>130 | Val | Ala | Ser | Asp | Thr<br>135 |
| Ser | Asp | Cys | Val | Leu<br>140 | Ser | Ser | Thr | Leu | Gly<br>145 | Pro | Glu | Lys | Asp | Ser<br>150 | Arg |
| Val | Ser | Val | Thr<br>155 | Lys | Pro | Phe | Met | Leu<br>160 | Pro | Pro | Val | Ala | Ala<br>165 | Ser | Ser |
| Leu | Arg | Asn<br>170 | Asp | Ser | Ser | Ser | Ser<br>175 | Asn |

( 2 ) INFORMATION FOR SEQ ID NO:5:

( i ) SEQUENCE CHARACTERISTICS:
        ( A ) LENGTH: 822 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 1..819

( i x ) FEATURE:
        ( A ) NAME/KEY: sig_peptide
        ( B ) LOCATION: 1..75

( i x ) FEATURE:
        ( A ) NAME/KEY: mat_peptide
        ( B ) LOCATION: 76..819

( x ) PUBLICATION INFORMATION:
        ( H ) DOCUMENT NUMBER: WO 91/05795 A1
        ( I ) FILING DATE: 28-SEP-1990
        ( J ) PUBLICATION DATE: 02-MAY-1991
        ( K ) RELEVANT RESIDUES IN SEQ ID NO:5: FROM 1 TO 822

( x i ) SEQUENCE DESCRIPTION: SEQ ID NO:5:

ATG AAG AAG ACA CAA ACT TGG ATT ATC ACT TGC ATT TAT CTT CAA CTG    48

```
Met Lys Lys Thr Gln Thr Trp Ile Ile Thr Cys Ile Tyr Leu Gln Leu
-25                 -20                 -15                 -10

CTC CTA TTT AAT CCT CTT GTC AAA ACC AAG GAG ATC TGC GGG AAT CCT     96
Leu Leu Phe Asn Pro Leu Val Lys Thr Lys Glu Ile Cys Gly Asn Pro
            -5                   1                   5

GTG ACT GAT AAT GTA AAA GAC ATT ACA AAA CTG GTG GCA AAT CTT CCA    144
Val Thr Asp Asn Val Lys Asp Ile Thr Lys Leu Val Ala Asn Leu Pro
        10                  15                  20

AAT GAC TAT ATG ATA ACC CTC AAC TAT GTC GCC GGG ATG GAT GTT TTG    192
Asn Asp Tyr Met Ile Thr Leu Asn Tyr Val Ala Gly Met Asp Val Leu
        25                  30                  35

CCT AGT CAT TGT TGG CTA CGA GAT ATG GTA ATA CAA TTA TCA CTC AGC    240
Pro Ser His Cys Trp Leu Arg Asp Met Val Ile Gln Leu Ser Leu Ser
40                  45                  50                  55

TTG ACT ACT CTT CTG GAC AAG TTC TCA AAT ATT TCT GAA GGC TTG AGT    288
Leu Thr Thr Leu Leu Asp Lys Phe Ser Asn Ile Ser Glu Gly Leu Ser
            60                  65                  70

AAT TAC TCC ATC ATA GAC AAA CTT GGG AAA ATA GTG GAT GAC CTC GTG    336
Asn Tyr Ser Ile Ile Asp Lys Leu Gly Lys Ile Val Asp Asp Leu Val
            75                  80                  85

TTA TGC ATG GAA GAA AAC GCA CCG AAG AAT ATA AAA GAA TCT CCG AAG    384
Leu Cys Met Glu Glu Asn Ala Pro Lys Asn Ile Lys Glu Ser Pro Lys
        90                  95                  100

AGG CCA GAA ACT AGA TCC TTT ACT CCT GAA GAA TTC TTT AGT ATT TTC    432
Arg Pro Glu Thr Arg Ser Phe Thr Pro Glu Glu Phe Phe Ser Ile Phe
105                 110                 115

AAT AGA TCC ATT GAT GCC TTT AAG GAC TTT ATG GTG GCA TCT GAC ACT    480
Asn Arg Ser Ile Asp Ala Phe Lys Asp Phe Met Val Ala Ser Asp Thr
120                 125                 130                 135

AGT GAC TGT GTG CTC TCT TCA ACA TTA GGT CCC GAG AAA GAT TCC AGA    528
Ser Asp Cys Val Leu Ser Ser Thr Leu Gly Pro Glu Lys Asp Ser Arg
                140                 145                 150

GTC AGT GTC ACA AAA CCA TTT ATG TTA CCC CCT GTT GCA GCC AGC TCC    576
Val Ser Val Thr Lys Pro Phe Met Leu Pro Pro Val Ala Ala Ser Ser
            155                 160                 165

CTT AGG AAT GAC AGC AGT AGC AGT AAT AGG AAA GCC GCA AAG GCC CCT    624
Leu Arg Asn Asp Ser Ser Ser Ser Asn Arg Lys Ala Ala Lys Ala Pro
        170                 175                 180

GAA GAC TCG GGC CTA CAA TGG ACA GCC ATG GCA TTG CCG GCT CTC ATT    672
Glu Asp Ser Gly Leu Gln Trp Thr Ala Met Ala Leu Pro Ala Leu Ile
185                 190                 195

TCG CTT GTA ATT GGC TTT GCT TTT GGA GCC TTA TAC TGG AAG AAG AAA    720
Ser Leu Val Ile Gly Phe Ala Phe Gly Ala Leu Tyr Trp Lys Lys Lys
200                 205                 210                 215

CAG TCA AGT CTT ACA AGG GCA GTT GAA AAT ATA CAG ATT AAT GAA GAG    768
Gln Ser Ser Leu Thr Arg Ala Val Glu Asn Ile Gln Ile Asn Glu Glu
            220                 225                 230

GAT AAT GAG ATA AGT ATG TTG CAA CAG AAA GAG AGA GAA TTT CAA GAG    816
Asp Asn Glu Ile Ser Met Leu Gln Gln Lys Glu Arg Glu Phe Gln Glu
            235                 240                 245

GTG TAA                                                            822
Val
```

( 2 ) INFORMATION FOR SEQ ID NO:6:

( i ) SEQUENCE CHARACTERISTICS:
        ( A ) LENGTH: 273 amino acids
        ( B ) TYPE: amino acid
        ( D ) TOPOLOGY: linear ( i i ) MOLECULE TYPE: protein ( i x ) FEATURE:
    ( A ) NAME/KEY: cleavage site
    ( B ) LOCATION: 164..165

( x i ) SEQUENCE DESCRIPTION: SEQ ID NO:6:

| Met -25 | Lys | Lys | Thr | Gln -20 | Thr | Trp | Ile | Ile | Thr -15 | Cys | Ile | Tyr | Leu | Gln -10 | Leu |
|---|---|---|---|---|---|---|---|---|---|---|---|---|---|---|---|
| Leu | Leu | Phe | Asn | Pro -5 | Leu | Val | Lys | Thr | Lys 1 | Glu | Ile | Cys | Gly 5 | Asn | Pro |
| Val | Thr | Asp 10 | Asn | Val | Lys | Asp | Ile 15 | Thr | Lys | Leu | Val | Ala 20 | Asn | Leu | Pro |
| Asn | Asp 25 | Tyr | Met | Ile | Thr | Leu 30 | Asn | Tyr | Val | Ala | Gly 35 | Met | Asp | Val | Leu |
| Pro 40 | Ser | His | Cys | Trp | Leu 45 | Arg | Asp | Met | Val | Ile 50 | Gln | Leu | Ser | Leu | Ser 55 |
| Leu | Thr | Thr | Leu | Leu 60 | Asp | Lys | Phe | Ser | Asn 65 | Ile | Ser | Glu | Gly | Leu 70 | Ser |
| Asn | Tyr | Ser | Ile 75 | Ile | Asp | Lys | Leu | Gly 80 | Lys | Ile | Val | Asp | Asp 85 | Leu | Val |
| Leu | Cys | Met 90 | Glu | Glu | Asn | Ala | Pro 95 | Lys | Asn | Ile | Lys | Glu 100 | Ser | Pro | Lys |
| Arg | Pro 105 | Glu | Thr | Arg | Ser | Phe 110 | Thr | Pro | Glu | Glu | Phe 115 | Phe | Ser | Ile | Phe |
| Asn 120 | Arg | Ser | Ile | Asp | Ala 125 | Phe | Lys | Asp | Phe | Met 130 | Val | Ala | Ser | Asp | Thr 135 |
| Ser | Asp | Cys | Val | Leu 140 | Ser | Ser | Thr | Leu | Gly 145 | Pro | Glu | Lys | Asp | Ser 150 | Arg |
| Val | Ser | Val | Thr 155 | Lys | Pro | Phe | Met | Leu 160 | Pro | Pro | Val | Ala | Ala 165 | Ser | Ser |
| Leu | Arg | Asn 170 | Asp | Ser | Ser | Ser | Ser 175 | Asn | Arg | Lys | Ala | Ala 180 | Lys | Ala | Pro |
| Glu | Asp 185 | Ser | Gly | Leu | Gln | Trp 190 | Thr | Ala | Met | Ala | Leu 195 | Pro | Ala | Leu | Ile |
| Ser 200 | Leu | Val | Ile | Gly | Phe 205 | Ala | Phe | Gly | Ala | Leu 210 | Tyr | Trp | Lys | Lys | Lys 215 |
| Gln | Ser | Ser | Leu | Thr 220 | Arg | Ala | Val | Glu | Asn 225 | Ile | Gln | Ile | Asn | Glu 230 | Glu |
| Asp | Asn | Glu | Ile 235 | Ser | Met | Leu | Gln | Gln 240 | Lys | Glu | Arg | Glu | Phe 245 | Gln | Glu |
| Val | | | | | | | | | | | | | | | |

( 2 ) INFORMATION FOR SEQ ID NO:7:

( i ) SEQUENCE CHARACTERISTICS:
        ( A ) LENGTH: 231 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x ) PUBLICATION INFORMATION:
        ( A ) AUTHORS: Lyman, et al.
        ( C ) JOURNAL: Cell
        ( F ) PAGES: 1157-1167

(G) DATE: 1993
(K) RELEVANT RESIDUES IN SEQ ID NO:7: FROM 1 TO 231

(xi) SEQUENCE DESCRIPTION: SEQ ID NO:7:

| Met | Thr | Val | Leu | Ala | Pro | Ala | Trp | Ser | Pro | Asn | Ser | Ser | Leu | Leu | Leu |
| 1 | | | | 5 | | | | | 10 | | | | | 15 | |
| Leu | Leu | Leu | Leu | Leu | Ser | Pro | Cys | Leu | Arg | Gly | Thr | Pro | Asp | Cys | Tyr |
| | | | 20 | | | | | 25 | | | | | 30 | | |
| Phe | Ser | His | Ser | Pro | Ile | Ser | Ser | Asn | Phe | Lys | Val | Lys | Phe | Arg | Glu |
| | | 35 | | | | | 40 | | | | | 45 | | | |
| Leu | Thr | Asp | His | Leu | Leu | Lys | Asp | Tyr | Pro | Val | Thr | Val | Ala | Val | Asn |
| | 50 | | | | | 55 | | | | | 60 | | | | |
| Leu | Gln | Asp | Glu | Lys | His | Cys | Lys | Ala | Leu | Trp | Ser | Leu | Phe | Leu | Ala |
| 65 | | | | | 70 | | | | | 75 | | | | | 80 |
| Gln | Arg | Trp | Ile | Glu | Gln | Leu | Lys | Thr | Val | Ala | Gly | Ser | Lys | Met | Gln |
| | | | | 85 | | | | | 90 | | | | | 95 | |
| Thr | Leu | Leu | Glu | Asp | Val | Asn | Thr | Glu | Ile | His | Phe | Val | Thr | Ser | Cys |
| | | | 100 | | | | | 105 | | | | | 110 | | |
| Thr | Phe | Gln | Pro | Leu | Pro | Glu | Cys | Leu | Arg | Phe | Val | Gln | Thr | Asn | Ile |
| | | 115 | | | | | 120 | | | | | 125 | | | |
| Ser | His | Leu | Leu | Lys | Asp | Thr | Cys | Thr | Gln | Leu | Leu | Ala | Leu | Lys | Pro |
| | 130 | | | | | 135 | | | | | 140 | | | | |
| Cys | Ile | Gly | Lys | Ala | Cys | Gln | Asn | Phe | Ser | Arg | Cys | Leu | Glu | Val | Gln |
| 145 | | | | | 150 | | | | | 155 | | | | | 160 |
| Cys | Gln | Pro | Asp | Ser | Ser | Thr | Leu | Leu | Pro | Pro | Arg | Ser | Pro | Ile | Ala |
| | | | | 165 | | | | | 170 | | | | | 175 | |
| Leu | Glu | Ala | Thr | Glu | Leu | Pro | Glu | Pro | Arg | Pro | Arg | Gln | Leu | Leu | Leu |
| | | | 180 | | | | | 185 | | | | | 190 | | |
| Leu | Leu | Leu | Leu | Leu | Pro | Leu | Thr | Leu | Val | Leu | Leu | Ala | Ala | Ala | Trp |
| | | 195 | | | | | 200 | | | | | 205 | | | |
| Gly | Leu | Arg | Trp | Gln | Arg | Ala | Arg | Arg | Lys | Gly | Glu | Leu | His | Pro | Gly |
| | 210 | | | | | 215 | | | | | 220 | | | | |
| Val | Pro | Leu | Pro | Ser | His | Pro | | | | | | | | | |
| 225 | | | | | 230 | | | | | | | | | | |